(12) United States Patent  (10) Patent No.: US 10,219,950 B2
Andreas et al.  (45) Date of Patent: Mar. 5, 2019

(54) FEATURES TO IMPROVE AND SENSE TYMPANIC MEMBRANE APPOSITION BY TYMPANOSTOMY TUBE DELIVERY INSTRUMENT

(71) Applicant: Tusker Medical, Inc., Menlo Park, CA (US)

(72) Inventors: Bernard H. Andreas, Redwood City, CA (US); Rohit Girotra, San Francisco, CA (US); Jeffrey A. Walker, Livermore, CA (US); T. Daniel Gross, Los Gatos, CA (US); Mathew D. Clopp, Santa Clara, CA (US); Mahyar Z. Kermani, San Ramon, CA (US); Scott J. Baron, Menlo Park, CA (US)

(73) Assignee: Tusker Medical, Inc., Menlo Park, CA (US)

( * ) Notice: Subject to any disclaimer, the term of this patent is extended or adjusted under 35 U.S.C. 154(b) by 369 days.

(21) Appl. No.: 15/090,353

(22) Filed: Apr. 4, 2016

(65) Prior Publication Data
US 2016/0213519 A1  Jul. 28, 2016

Related U.S. Application Data

(63) Continuation of application No. 13/804,553, filed on Mar. 14, 2013, now Pat. No. 9,320,652.

(51) Int. Cl.
 *A61F 11/00* (2006.01)
(52) U.S. Cl.
 CPC .................................. *A61F 11/002* (2013.01)

(58) Field of Classification Search
 CPC .. A61B 2017/1205; A61B 2017/12054; A61B 2017/12059; A61B 2017/12063;
 (Continued)

(56) References Cited

U.S. PATENT DOCUMENTS

| 885,673 A | 7/1907 | Roswell |
| 1,920,006 A | 7/1933 | Dozier et al. |

(Continued)

FOREIGN PATENT DOCUMENTS

| CN | 86105171 A | 3/1987 |
| DE | 19618585 | 11/1997 |

(Continued)

OTHER PUBLICATIONS

Patent Examination Report No. 1 for Australian Patent Application No. 2013209354, dated Oct. 13, 2014, 5 pages.

(Continued)

*Primary Examiner* — Wade Miles

(57) ABSTRACT

A tympanostomy tube delivery device comprises a shaft assembly, a pressure equalization tube, and a sensor. The shaft assembly comprises a cannula and a pusher operable to translate relative to the cannula. The pressure equalization tube is positioned within the shaft assembly. The pusher is operable to drive the pressure equalization tube out of the shaft assembly. The sensor is operable to detect a physical parameter associated with engagement between the distal end of the shaft assembly and a tympanic membrane. A controller may activate a feedback device to inform an operator that the distal end of the shaft assembly has achieved suitable apposition with the tympanic membrane, based on information from the sensor.

18 Claims, 27 Drawing Sheets

(58) Field of Classification Search
CPC ........... A61B 2017/12068; A61B 2017/12072; A61B 2017/12077; A61B 2017/12081; A61B 2017/12086; A61B 2017/1209; A61B 2017/12095; A61B 2017/00672; A61F 11/002; A61F 2002/183; A61F 11/00; A61F 2/95; A61F 2002/9505; A61F 2002/9511; A61F 2002/9522; A61F 2002/9528; A61F 2002/9534; A61F 2/954; A61F 2/958; A61F 2002/9583; A61F 2002/9586; A61F 2/962; A61F 2/966; A61F 2002/9665; A61F 2/97

See application file for complete search history.

(56) References Cited

U.S. PATENT DOCUMENTS

| | | |
|---|---|---|
| 2,162,681 A | 6/1939 | Ryan |
| 3,473,170 A | 10/1969 | Haase et al. |
| 3,638,643 A | 2/1972 | Hotchkiss |
| 3,741,197 A | 6/1973 | Sanz et al. |
| 3,807,404 A | 4/1974 | Weissman et al. |
| 3,888,258 A | 6/1975 | Akiyama |
| 3,897,786 A | 8/1975 | Garnett et al. |
| 3,913,584 A | 10/1975 | Walchle et al. |
| 3,948,271 A | 4/1976 | Akiyama |
| 3,991,755 A | 11/1976 | Vernon et al. |
| 4,168,697 A | 9/1979 | Cantekin |
| 4,335,713 A | 6/1982 | Komiya |
| 4,335,715 A | 6/1982 | Kirkley |
| 4,380,998 A | 4/1983 | Kieffer, III et al. |
| 4,406,282 A | 9/1983 | Parker et al. |
| 4,468,218 A | 8/1984 | Armstrong |
| 4,473,073 A | 9/1984 | Darnell |
| 4,552,137 A | 11/1985 | Strauss |
| 4,564,009 A | 1/1986 | Brinkhoff |
| 4,712,537 A | 12/1987 | Pender |
| 4,750,491 A | 6/1988 | Kaufman et al. |
| 4,796,624 A | 1/1989 | Trott et al. |
| 4,800,876 A | 1/1989 | Fox et al. |
| 4,913,132 A | 4/1990 | Gabriel |
| 4,946,440 A | 8/1990 | Hall |
| 4,964,850 A | 10/1990 | Bouton et al. |
| 4,968,296 A | 11/1990 | Ritch et al. |
| 4,971,076 A | 11/1990 | Densert et al. |
| 5,026,378 A | 6/1991 | Goldsmith, III |
| 5,044,373 A | 9/1991 | Northeved et al. |
| 5,047,007 A | 9/1991 | McNichols et al. |
| 5,053,040 A | 10/1991 | Goldsmith, III |
| 5,092,837 A | 3/1992 | Ritch et al. |
| 5,107,861 A | 4/1992 | Narboni |
| 5,135,478 A | 8/1992 | Sibalis |
| 5,158,540 A | 10/1992 | Wijay |
| 5,178,623 A | 1/1993 | Cinberg et al. |
| 5,254,120 A | 10/1993 | Cinberg et al. |
| 5,261,903 A | 11/1993 | Dhaliwal et al. |
| D352,780 S | 11/1994 | Glaeser et al. |
| 5,370,656 A | 12/1994 | Shevel |
| 5,421,818 A | 6/1995 | Arenberg |
| 5,466,239 A | 11/1995 | Cinberg et al. |
| 5,489,286 A | 2/1996 | Cinberg et al. |
| 5,496,329 A | 3/1996 | Reisinger |
| D378,611 S | 3/1997 | Croley |
| 5,610,988 A | 3/1997 | Miyahara |
| 5,643,280 A | 7/1997 | Del Rio et al. |
| 5,645,584 A | 7/1997 | Suyama |
| 5,658,235 A | 8/1997 | Priest et al. |
| 5,674,196 A | 10/1997 | Donaldson et al. |
| 5,676,635 A | 10/1997 | Levin |
| 5,681,323 A | 10/1997 | Arick |
| D387,863 S | 12/1997 | Herman et al. |
| 5,707,383 A | 1/1998 | Bays et al. |
| 5,775,336 A | 7/1998 | Morris |
| 5,782,744 A * | 7/1998 | Money ................. H04R 25/606 600/25 |
| 5,792,100 A | 8/1998 | Shantha |
| 5,810,848 A | 9/1998 | Hayhurst |
| 5,827,295 A | 10/1998 | Del Rio et al. |
| 5,893,828 A | 4/1999 | Uram |
| 5,893,837 A | 4/1999 | Eagles et al. |
| 5,984,930 A | 11/1999 | Maciunas et al. |
| D418,223 S | 12/1999 | Phipps et al. |
| D420,741 S | 2/2000 | Croley |
| 6,022,342 A | 2/2000 | Mukherjee |
| 6,024,726 A * | 2/2000 | Hill ........................ A61F 11/00 604/117 |
| 6,039,748 A | 3/2000 | Savage et al. |
| 6,045,528 A | 4/2000 | Arenberg et al. |
| D424,197 S | 5/2000 | Sydlowski et al. |
| 6,059,803 A | 5/2000 | Spilman |
| D426,135 S | 6/2000 | Lee |
| 6,077,179 A | 6/2000 | Liechty, II |
| 6,110,196 A | 8/2000 | Edwards |
| 6,137,889 A | 10/2000 | Shennib et al. |
| 6,171,236 B1 | 1/2001 | Bonutti |
| 6,183,469 B1 | 2/2001 | Thapliyal et al. |
| 6,200,280 B1 | 3/2001 | Brenneman et al. |
| 6,206,888 B1 | 3/2001 | Bicek et al. |
| 6,245,077 B1 | 6/2001 | East et al. |
| 6,248,112 B1 | 6/2001 | Gambale et al. |
| 6,251,121 B1 | 6/2001 | Saadat |
| 6,258,067 B1 | 7/2001 | Hill |
| D450,843 S | 11/2001 | McGuckin, Jr. et al. |
| 6,319,199 B1 | 11/2001 | Sheehan et al. |
| 6,358,231 B1 | 3/2002 | Schindler et al. |
| 6,416,512 B1 | 7/2002 | Ellman et al. |
| 6,398,758 B1 | 8/2002 | Jacobsen et al. |
| 6,440,102 B1 | 8/2002 | Arenberg et al. |
| 6,447,522 B2 | 9/2002 | Gambale et al. |
| 6,475,138 B1 | 11/2002 | Schechter et al. |
| 6,512,950 B2 | 1/2003 | Li et al. |
| 6,514,261 B1 | 2/2003 | Randall et al. |
| 6,520,939 B2 | 2/2003 | Lafontaine |
| 6,522,827 B1 | 2/2003 | Loeb et al. |
| 6,553,253 B1 | 4/2003 | Chang |
| 6,645,173 B1 | 11/2003 | Liebowitz |
| 6,648,873 B2 | 11/2003 | Arenberg et al. |
| 6,663,575 B2 | 12/2003 | Leysieffer |
| 6,682,558 B2 | 1/2004 | Tu et al. |
| 6,770,080 B2 | 8/2004 | Kaplan et al. |
| 6,916,159 B2 | 7/2005 | Rush |
| 6,962,595 B1 | 11/2005 | Chamness et al. |
| 7,127,285 B2 | 10/2006 | Henley et al. |
| 7,137,975 B2 | 11/2006 | Miller et al. |
| D535,027 S | 1/2007 | James et al. |
| 7,160,274 B2 | 1/2007 | Ciok et al. |
| 7,344,507 B2 | 3/2008 | Briggs et al. |
| 7,351,246 B2 | 4/2008 | Epley |
| 7,381,210 B2 | 6/2008 | Zarbatany et al. |
| D595,410 S | 6/2009 | Luzon |
| 7,563,232 B2 | 7/2009 | Freeman et al. |
| D598,543 S | 8/2009 | Vogel et al. |
| 7,654,997 B2 | 2/2010 | Makower et al. |
| 7,677,734 B2 | 3/2010 | Wallace |
| 7,704,259 B2 | 4/2010 | Kaplan et al. |
| 7,749,254 B2 | 7/2010 | Sobelman et al. |
| D622,842 S | 8/2010 | Benoist |
| D640,374 S | 6/2011 | Liu et al. |
| 8,052,693 B2 | 11/2011 | Shahoian |
| 8,192,420 B2 | 6/2012 | Morriss et al. |
| 8,249,700 B2 | 8/2012 | Clifford et al. |
| 8,282,648 B2 | 10/2012 | Tekulve |
| 8,409,175 B2 | 4/2013 | Lee et al. |
| 8,425,488 B2 | 4/2013 | Clifford et al. |
| 8,498,425 B2 | 7/2013 | Graylin |
| 8,518,098 B2 | 8/2013 | Roeder et al. |
| 8,702,722 B2 | 4/2014 | Shahoian |
| 8,840,602 B2 | 9/2014 | Morriss et al. |
| 8,849,394 B2 | 9/2014 | Clifford et al. |
| 8,864,774 B2 | 10/2014 | Liu et al. |
| 8,998,927 B2 | 4/2015 | Kaplan et al. |
| 9,011,363 B2 | 4/2015 | Clopp et al. |
| 9,023,059 B2 | 5/2015 | Loushin et al. |
| 9,216,112 B2 | 12/2015 | Clifford et al. |

(56) References Cited

U.S. PATENT DOCUMENTS

| | | |
|---|---|---|
| 9,320,652 B2 | 4/2016 | Andreas et al. |
| 9,387,124 B2 | 7/2016 | Clifford |
| 9,539,146 B2 | 1/2017 | Girotra et al. |
| 9,681,891 B2 | 6/2017 | Andreas et al. |
| 9,707,131 B2 | 7/2017 | Shahoian |
| 9,770,366 B2 | 9/2017 | Liu et al. |
| 9,833,359 B2 | 12/2017 | Clopp |
| 9,833,360 B2 | 12/2017 | Andreas et al. |
| 9,833,601 B2 | 12/2017 | Clifford |
| 2001/0020173 A1 | 9/2001 | Klumb et al. |
| 2002/0026125 A1 | 2/2002 | Leysieffer |
| 2002/0069883 A1 | 6/2002 | Hirchenbain |
| 2002/0111585 A1 | 8/2002 | Lafontaine |
| 2002/0138091 A1 | 9/2002 | Pflueger |
| 2002/0161379 A1* | 10/2002 | Kaplan ............... A61F 11/002 606/109 |
| 2002/0169456 A1 | 11/2002 | Tu et al. |
| 2003/0018291 A1 | 1/2003 | Hill et al. |
| 2003/0040717 A1 | 2/2003 | Saulenas et al. |
| 2003/0060799 A1 | 3/2003 | Arenberg et al. |
| 2003/0097178 A1* | 5/2003 | Roberson ............... A61F 2/18 623/10 |
| 2003/0120292 A1 | 6/2003 | Park et al. |
| 2003/0187456 A1 | 10/2003 | Perry |
| 2003/0199791 A1 | 10/2003 | Boecker et al. |
| 2004/0054339 A1 | 3/2004 | Ciok et al. |
| 2004/0064024 A1 | 4/2004 | Sommer |
| 2005/0033343 A1* | 2/2005 | Chermoni ......... A61M 25/0122 606/191 |
| 2005/0165368 A1 | 7/2005 | Py et al. |
| 2005/0182385 A1 | 8/2005 | Epley |
| 2005/0187546 A1* | 8/2005 | Bek ................... A61B 18/1492 606/41 |
| 2005/0203552 A1 | 9/2005 | Laufer et al. |
| 2005/0235422 A1 | 10/2005 | Wallace |
| 2005/0240147 A1 | 10/2005 | Makower et al. |
| 2006/0004323 A1 | 1/2006 | Chang et al. |
| 2006/0095050 A1 | 5/2006 | Hartley et al. |
| 2006/0142700 A1 | 6/2006 | Sobelman et al. |
| 2006/0155304 A1 | 7/2006 | Kaplan et al. |
| 2006/0161218 A1 | 7/2006 | Danilov |
| 2006/0163313 A1 | 7/2006 | Larson |
| 2006/0282062 A1 | 12/2006 | Ishikawa et al. |
| 2007/0088247 A1 | 4/2007 | Bliweis et al. |
| 2007/0233222 A1 | 10/2007 | Roeder et al. |
| 2007/0276466 A1 | 11/2007 | Lavelle et al. |
| 2008/0027423 A1 | 1/2008 | Choi et al. |
| 2008/0051804 A1 | 2/2008 | Cottler et al. |
| 2008/0065011 A1 | 3/2008 | Marchand et al. |
| 2008/0212416 A1 | 9/2008 | Polonio et al. |
| 2008/0262468 A1 | 10/2008 | Clifford et al. |
| 2008/0262508 A1 | 10/2008 | Clifford et al. |
| 2008/0262510 A1 | 10/2008 | Clifford |
| 2009/0163828 A1 | 6/2009 | Turner et al. |
| 2009/0171271 A1 | 7/2009 | Webster et al. |
| 2009/0209972 A1 | 8/2009 | Loushin et al. |
| 2009/0299344 A1 | 12/2009 | Lee et al. |
| 2009/0299379 A1 | 12/2009 | Katz et al. |
| 2009/0299433 A1 | 12/2009 | Lee |
| 2010/0041447 A1 | 2/2010 | Graylin |
| 2010/0048978 A1 | 2/2010 | Sing et al. |
| 2010/0061581 A1 | 3/2010 | Soetejo et al. |
| 2010/0160819 A1 | 6/2010 | Parihar et al. |
| 2010/0198135 A1 | 8/2010 | Morriss et al. |
| 2010/0217296 A1 | 8/2010 | Morriss et al. |
| 2010/0274188 A1 | 10/2010 | Chang et al. |
| 2010/0324488 A1 | 12/2010 | Smith |
| 2011/0015645 A1 | 1/2011 | Liu et al. |
| 2011/0022069 A1 | 1/2011 | Mitusina |
| 2011/0077579 A1* | 3/2011 | Harrison ........... A61M 5/14276 604/20 |
| 2011/0288559 A1 | 11/2011 | Shahoian |
| 2012/0179187 A1 | 7/2012 | Loushin et al. |
| 2012/0265097 A1 | 10/2012 | Melchiorri et al. |
| 2012/0283563 A1 | 11/2012 | Moore et al. |
| 2012/0310145 A1 | 12/2012 | Clifford et al. |
| 2013/0030456 A1 | 1/2013 | Assell et al. |
| 2013/0090544 A1 | 4/2013 | Clifford et al. |
| 2013/0338678 A1 | 12/2013 | Loushin et al. |
| 2014/0094733 A1 | 4/2014 | Clopp et al. |
| 2014/0100584 A1 | 4/2014 | Konstorum et al. |
| 2014/0194891 A1 | 7/2014 | Shahoian |
| 2014/0276906 A1 | 9/2014 | Andreas et al. |
| 2014/0277050 A1 | 9/2014 | Andreas et al. |
| 2015/0142029 A1 | 5/2015 | Fahn et al. |
| 2015/0164695 A1 | 6/2015 | Liu et al. |
| 2015/0209509 A1 | 7/2015 | O'Cearbhaill et al. |
| 2015/0305944 A1 | 10/2015 | Kaplan et al. |
| 2015/0320550 A1* | 11/2015 | Downing ............. A61N 1/0541 607/137 |
| 2016/0038341 A1 | 2/2016 | Clopp et al. |
| 2016/0038342 A1 | 2/2016 | Van et al. |
| 2016/0045369 A1 | 2/2016 | Clopp |
| 2016/0045370 A1 | 2/2016 | Andreas et al. |
| 2016/0045371 A1 | 2/2016 | Girotra et al. |
| 2017/0209310 A1 | 7/2017 | Girotra et al. |
| 2017/0281230 A1 | 10/2017 | Andreas et al. |
| 2018/0055693 A1 | 3/2018 | Liu et al. |
| 2018/0085258 A1 | 3/2018 | Andreas et al. |
| 2018/0085563 A1 | 3/2018 | Clifford et al. |
| 2018/0116876 A1 | 5/2018 | Clopp |

FOREIGN PATENT DOCUMENTS

| | | |
|---|---|---|
| DE | 19918288 A1 | 10/2000 |
| EP | 0214527 A1 | 3/1987 |
| FR | 2526656 | 11/1983 |
| JP | H 07-116190 A | 5/1995 |
| WO | WO 1999/011175 A1 | 3/1999 |
| WO | WO 2006/119512 | 11/2006 |
| WO | WO 2008/030485 | 3/2008 |
| WO | WO 2008/036368 | 3/2008 |
| WO | WO 2008/131195 | 10/2008 |
| WO | WO 2009/010788 | 1/2009 |
| WO | WO 2009/105619 | 8/2009 |
| WO | WO 2011/008948 | 1/2011 |
| WO | WO 2014/075949 | 5/2014 |
| WO | WO 2014/143543 | 9/2014 |
| WO | WO 2014/158571 | 10/2014 |
| WO | WO 2016/022899 | 2/2016 |
| WO | WO 2016/025308 | 2/2016 |
| WO | WO 2016/025309 | 2/2016 |
| WO | WO 2016/025310 | 2/2016 |
| WO | WO 2016/025453 | 2/2016 |

OTHER PUBLICATIONS

First Office Action for Chinese Patent Application No. 200880020861.9, dated Jul. 12, 2011, 10 pages.
Second Office Action for Chinese Patent Application No. 200880020861.9, dated Dec. 31, 2011, 3 pages.
Search Report for Chinese Patent Application No. 201310047126.X, dated Mar. 6, 2015, 2 pages.
Second Office Action for Chinese Patent Application No. 201310047126.X, dated Mar. 16, 2015, 10 pages.
Office Action for European Application No. 08746237.0, dated Mar. 24, 2016, 3 pages.
Office Action for European Application No. 08746237.0, dated Aug. 4, 2015, 7 pages.
Supplementary Partial Search Report for European Application No. 08746237.0, dated Jun. 30, 2014, 9 pages.
Notification of Reasons for Refusal for Japanese Patent Application No. 2010-504267, dated Nov. 20, 2012, 4 pages.
Notification of Reasons for Refusal for Japanese Patent Application No. 2010-504267, dated Nov. 12, 2013, 4 pages.
International Search Report for International Application No. PCT/US2008/060779, dated Sep. 3, 2008.
Written Opinion for International Application No. PCT/US2008/060779, dated Sep. 3, 2008.

(56) References Cited

OTHER PUBLICATIONS

International Preliminary Report on Patentability for International Application No. PCT/US2008/060779, dated Nov. 17, 2009.
Office Action for U.S. Appl. No. 11/749,729, dated May 26, 2011, 11 pages.
Office Action for U.S. Appl. No. 11/749,729, dated Jun. 17, 2010, 8 pages.
Office Action for U.S. Appl. No. 11/749,733, dated Jun. 10, 2009, 13 pages.
Office Action for U.S. Appl. No. 11/749,733, dated Dec. 2, 2008, 9 pages.
U.S. Appl. No. 61/085,360, filed Jul. 31, 2008.
International Search Report for International Application No. PCT/US2009/052395, dated Nov. 6, 2009.
Written Opinion for International Application No. PCT/US2009/052395, dated Nov. 6, 2009.
International Search Report for International Application No. PCT/US2010/058718, dated Feb. 17, 2011.
Written Opinion for International Application No. PCT/US2010/058718, dated Feb. 17, 2011.
U.S. Appl. No. 61/225,893, filed Jul. 15, 2009.
Patent Examination Report No. 1 for Australian Application No. 2010273372, dated Nov. 12, 2014, 2 pages.
First Office Action for Chinese Application No. 201080041755.6, dated Jul. 3, 2013.
Notification of Reasons for Refusal for Japanese Application No. 2012-520778, dated Feb. 18, 2014.
Communication of the Substantive Examination Report for Mexican Application No. MX/a/2012/000691, dated Apr. 24, 2014.
International Search Report for International Application No. PCT/US2010/042128, dated Aug. 27, 2010.
Written Opinion International Application No. PCT/US2010/042128, dated Aug. 27, 2010.
International Preliminary Report on Patentability for International Application No. PCT/US2010/042128, dated Jan. 17, 2012.
European Search Report for European Application No. 13173409.7, dated Sep. 16, 2013.
Search Report and Written Opinion for International Patent Application No. PCT/US2015/044179, dated Dec. 18, 2015, 15 pages.
Office Action for U.S. Appl. No. 13/804,553, dated Apr. 20, 2015, 11 pages.
International Search Report and Written Opinion for International Application No. PCT/US2014/018320, dated Jun. 2, 2014, 10 pages.
International Search Report and Written Opinion for International Application No. PCT/US2014/018347, dated Apr. 17, 2014, 9 pages.
International Search Report and Written Opinion for International Application No. PCT/US2015/044173, dated Oct. 12, 2015, 9 pages.
International Search Report and Written Opinion for International Application No. PCT/US2015/044177, dated Oct. 30, 2015, 10 pages.
International Search Report and Written Opinion for International Application No. PCT/US2015/044183, dated Nov. 4, 2015, 9 pages.
International Search Report and Written Opinion for International Application No. PCT/US2015/044610, dated Nov. 5, 2015, 12 pages.
International Search Report for International Application No. PCT/US2009/069388, dated Jun. 30, 2010.
Written Opinion for International Application No. PCT/US2009/069388, dated Jun. 30, 2010.
Comeau, M. et al., "Local Anesthesia of the Ear by Iontophoresis," vol. 98, Arch. Otolaryngol., pp. 114-120 (Aug. 1973).
Comeau, M. et al., "Anesthesia of the Human Tympanic Membrane by Iontophoresis of a Local Anesthetic," The Larynogoscope, vol. 88, pp. 277-285 (1978).
Echols, D. F. et al., "Anesthesia of the Ear by Iontophoresis of Lidocaine," Arch. Otolaryngol., vol. 101, pp. 418-421 (Jul. 1975).
Epley, J. M., "Modified Technique of Iontophoretic Anesthesia for Myringotomy in Children," Arch. Otolaryngol., vol. 103, pp. 358-360 (Jun. 1977).
Hasegawa, M. et al., "Iontophorectic anaesthesia of the tympanic membrane," Clinical Otolaryngoloy, vol. 3, pp. 63-66 (1978).
Ramsden, R. T. et al., "Anaesthesia of the tympanic membrane using iontophoresis," The Journal of Laryngology and Otology, 56(9):779-785 (Sep. 1977).
"Definition of Plenum," Compact Oxford English Dictionary [online], Retrieved from the Internet: <http://oxforddictionaries.com/definition/english/plenum>, Retrieved on Aug. 6, 2012, 2 pages.
"Definition of Plenum," Merriam-Webster's Online Dictionary, 11th Edition [online], Retrieved from the Internet: <http://www.merriam-webster.com/dictionary/plenum>, Retrieved on Aug. 14, 2012, 1 page.
Medtronic XOMED, "Activent® Antimicrobial Ventilation Tubes," Rev. 1.1, pp. 1-4, 2002, Jacksonville, FL.
Micromedics Innovative Surgical Products, "Micromedics Tympanostomy Tubes," [online], Retrieved on Jul. 15, 2010, Retrieved from the Internet <URL: http://www.micromedics-usa.com/products/otology/micromedicstubes.htm>, 7 pages.
Armstrong, "A New Treatment for Chronic Secretory Otitis Media" A.M.A. Archives of Otolaryngology, pp. 653-654 (1954).
Feuerstein, "A Split-Tube Prosthesis in Serous Otitis Media" Sixty-ninth Annual Session of the American Academy of Ophthalmology and Otolaryngology, Oct. 18-23, 1964, Chicago, IL, pp. 343-344.
Jurgens. et al., "Three New Middle Ear Ventilation Tubes" Seventy-sixth Annual Session of the American Academy of Ophthalmology and Otolaryngology, Sep. 20-24, 1971, Las Vegas, NV, pp. 1017-1019 (1971).
Lindeman et al., The "Arrow Tube" Residents in Otolaryngology, Massachusetts Eye and Ear Infirmary, 1 page (1964).
Pappas, "Middle Ear Ventilation Tubes" Meeting of the Southern Section of the American Laryngological, Rhinological and Otological Society, Inc., Williamsburg, VA, Jan. 12, 1974, pp. 1098-1117.
Per-Lee, "A Wide Flanged Middle Ear Ventilation Tube" Seventy-first Annual Session of the American Academy of Ophthalmology and Otolaryngology, Oct. 16-21, 1966, Chicago, IL, pp. 358-359.
Reuter, "The Stainless Bobbin Middle Ear Ventilation Tube" Seventy-second Annual Session of the American Academy of Ophthalmology and Otolaryngology, Oct. 29-Nov. 3, 1967, Chicago, IL, pp. 121-122.
Ringenberg, "A New Middle Ear Ventilation Device" Seventy-second Annual Session of the American Academy of Ophthalmology and Otolaryngology, Oct. 29-Nov. 3, 1967, Chicago, IL, 1 page.
Schmidt et al. "Transtympanic Aeration of the Middle Ear With Blocked Eustachian Tube" Acta Otolaryng., pp. 277-282 (1965).
Sheehy, "Collar Button Tube for Chronic Serous Otitis" Sixty-eighth Annual Session of the American Academy of Ophthalmology and Otolaryngology, Oct. 20-25, 1963, New York, NY, pp. 888-889.
Santa Barbara Medco, Inc. "Otological Ventilation Tubes" Product Brochure from http://www.sbmedco.com/ptfe_shepard.asp, 8 pages (Feb. 11, 2001).
Rhinology Products, Boston Medical Products, www.bosmed.com [date of publication unknown], pp. 1-16.
Office Action for U.S. Appl. No. 16/017,239, dated Sep. 18, 2018, 11 pages.

* cited by examiner

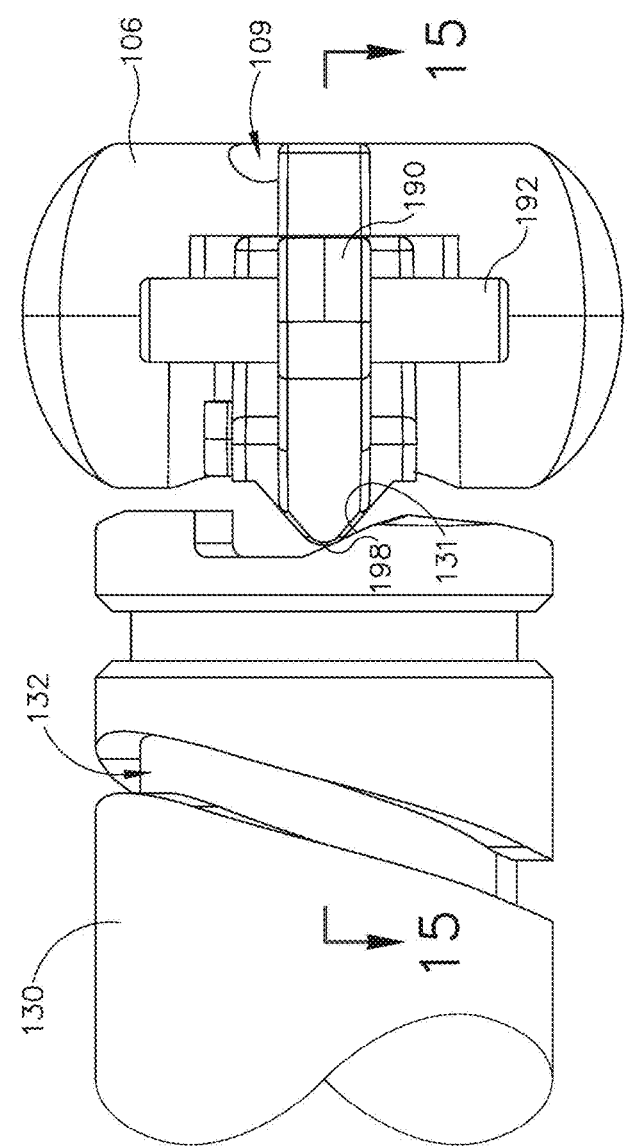

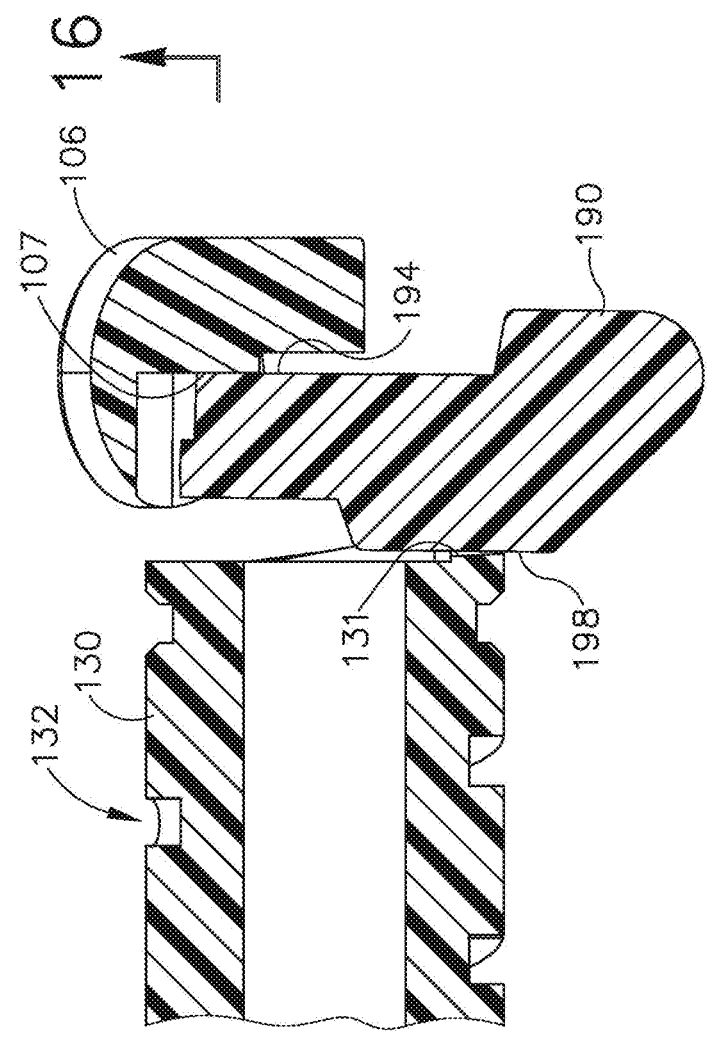

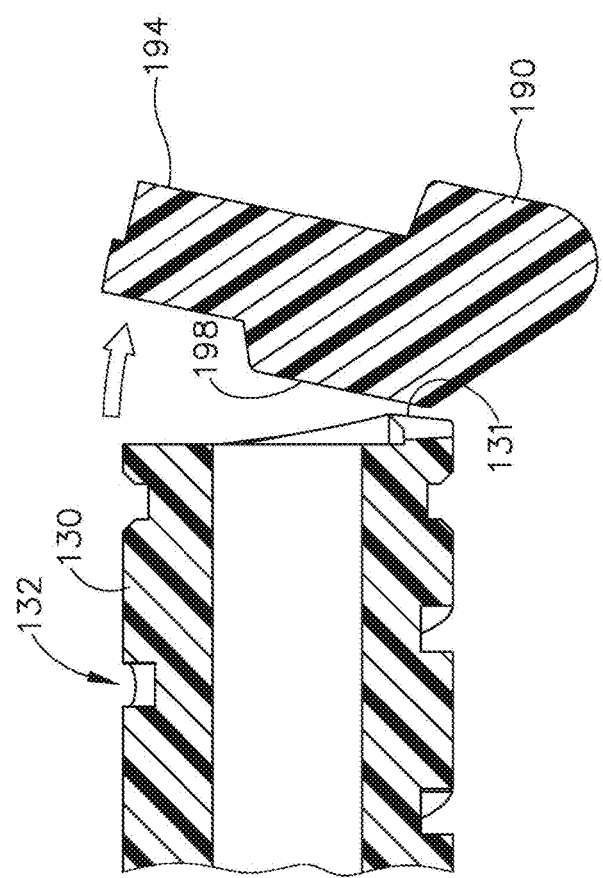

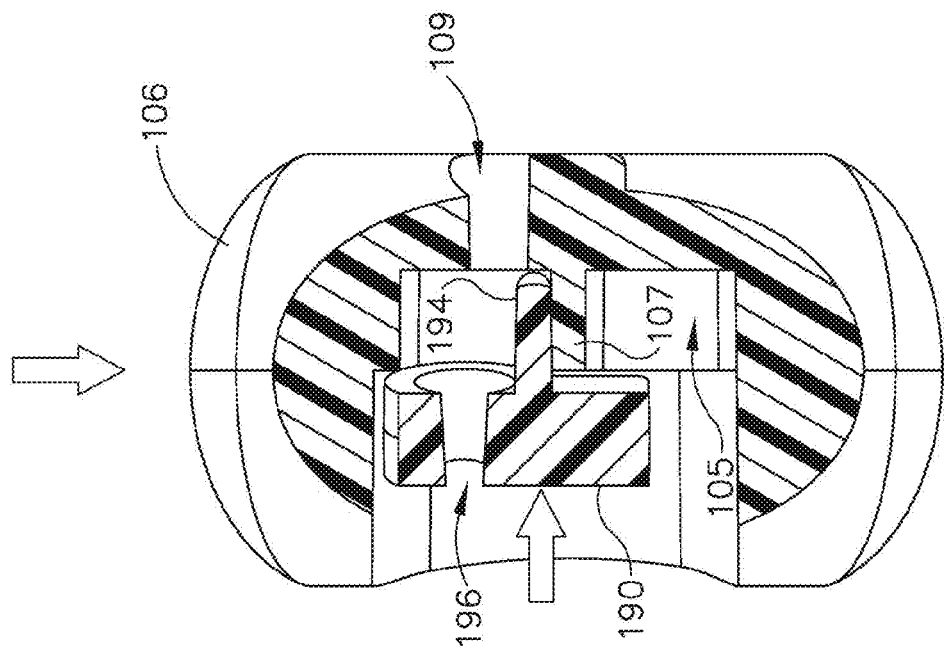
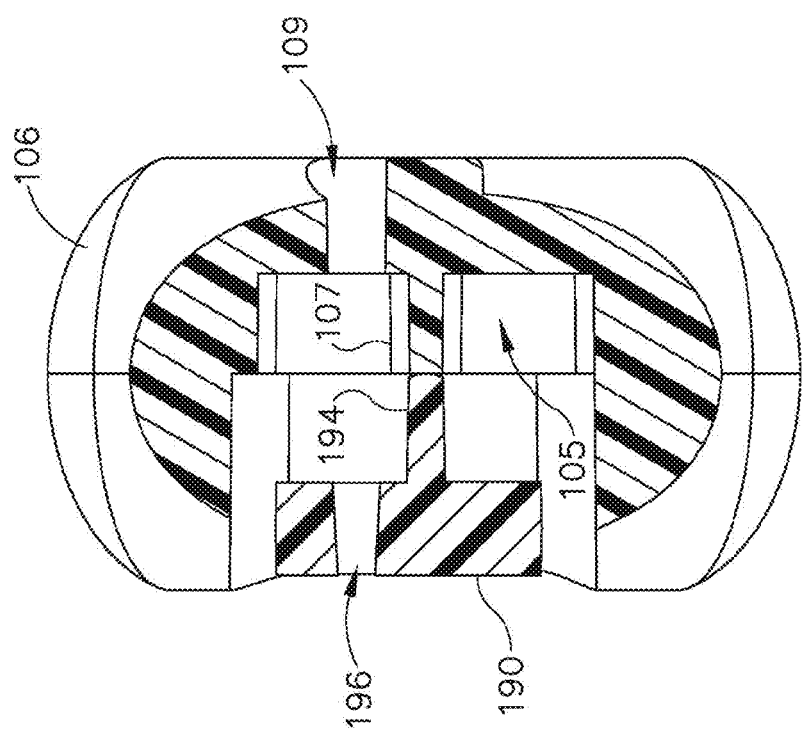
Fig. 16A
Fig. 16B

FEATURES TO IMPROVE AND SENSE TYMPANIC MEMBRANE APPOSITION BY TYMPANOSTOMY TUBE DELIVERY INSTRUMENT

CROSS-REFERENCE TO RELATED APPLICATION

This application is a continuation of U.S. patent application Ser. No. 13/804,553, entitled, "Features to Improve and Sense Tympanic Membrane Apposition by Tympanostomy Tube Delivery Instrument," filed Mar. 14, 2013, the disclosure of which is hereby incorporated by reference herein in its entirety.

BACKGROUND

Some children may exhibit recurrent episodes of otitis media and/or -otitis media with effusion. Treatment of severe cases may involve the placement of a pressure equalization tube or tympanostomy tube through the tympanic membrane to provide adequate drainage of the middle ear by providing fluid communication between the middle and outer ear. In particular, such a tube may provide a vent path that promotes drainage of fluid from the middle ear via the Eustachian tube and may thus reduce stress imposed on the tympanic membrane from pressure within the middle ear. This may further reduce the likelihood of future infections and pressure induced ruptures of the tympanic membrane. Pressure equalization tubes may fall out spontaneously within about a year of placement. Exemplary pressure equalization tube delivery systems are disclosed in U.S. Pat. No. 8,052,693, entitled "System and Method for the Simultaneous Automated Bilateral Delivery of Pressure Equalization Tubes," issued Nov. 8, 2011, the disclosure of which is incorporated by reference herein. Additional exemplary pressure equalization tube delivery systems are disclosed in U.S. Pat. No. 8,249,700, entitled "System and Method for the Simultaneous Bilateral Integrated Tympanic Drug Delivery and Guided Treatment of Target Tissues within the Ears," issued Aug. 21, 2012, the disclosure of which is incorporated by reference herein. Still additional exemplary pressure equalization tube delivery systems are disclosed in U.S. Pub. No. 2011/0015645, entitled "Tympanic Membrane Pressure Equalization Tube Delivery System," published Jan. 20, 2011, now U.S. Pat. No. 8,864,774, issued Oct. 21, 2014, the disclosure of which is incorporated by reference herein.

Insertion of a pressure equalization tube may be performed using general anesthesia in some cases, which may require additional resources such as an operating room, the presence of an anesthesiologist, and time in a recovery room. Furthermore, the use of general anesthesia may include certain risks that a patient may or may not be comfortable with undertaking. Some pressure equalization tube delivery systems and methods provide a local anesthetic through iontophoresis. Examples of such systems and methods are disclosed in U.S. Pub. No. 2010/0198135, entitled "Systems and Methods for Anesthetizing Ear Tissue," published Aug. 5, 2010, now U.S. Pat. No. 8,840,602, issued Sep. 23, 2014, the disclosure of which is incorporated by reference herein. Additional examples of such systems and methods are disclosed in U.S. Pat. No. 8,192,420, entitled "Iontophoresis Methods," issued Jun. 5, 2012, the disclosure of which is incorporated by reference herein.

While a variety of pressure equalization tube delivery systems and methods have been made and used, it is believed that no one prior to the inventor(s) has made or used an invention as described herein.

BRIEF DESCRIPTION OF THE DRAWINGS

It is believed the present invention will be better understood from the following description of certain examples taken in conjunction with the accompanying drawings, in which like reference numerals identify the same elements and in which:

FIG. 14 depicts a bottom plan view of the trigger mechanism of FIG. 10, showing the pawl engaged with the camshaft;

FIG. 15A depicts a cross-sectional view of the trigger mechanism of FIG. 10, taken along line 15-15 of FIG. 14, showing the pawl engaged with the camshaft;

FIG. 15B depicts a cross-sectional view of the trigger mechanism of FIG. 10, taken along line 15-15 of FIG. 14, showing the pawl disengaged from the camshaft, with the button actuator omitted;

FIG. 16A depicts a cross-sectional view of the pawl and button actuator of FIGS. 11 and 13, taken along line 16-16 of FIG. 15A, showing the button actuator arresting the pawl;

FIG. 16B depicts a cross-sectional view of the pawl and button actuator of FIGS. 11 and 13, taken along line 16-16 of FIG. 15A, showing the button actuator translated laterally to enable movement of the pawl;

Figure 1:
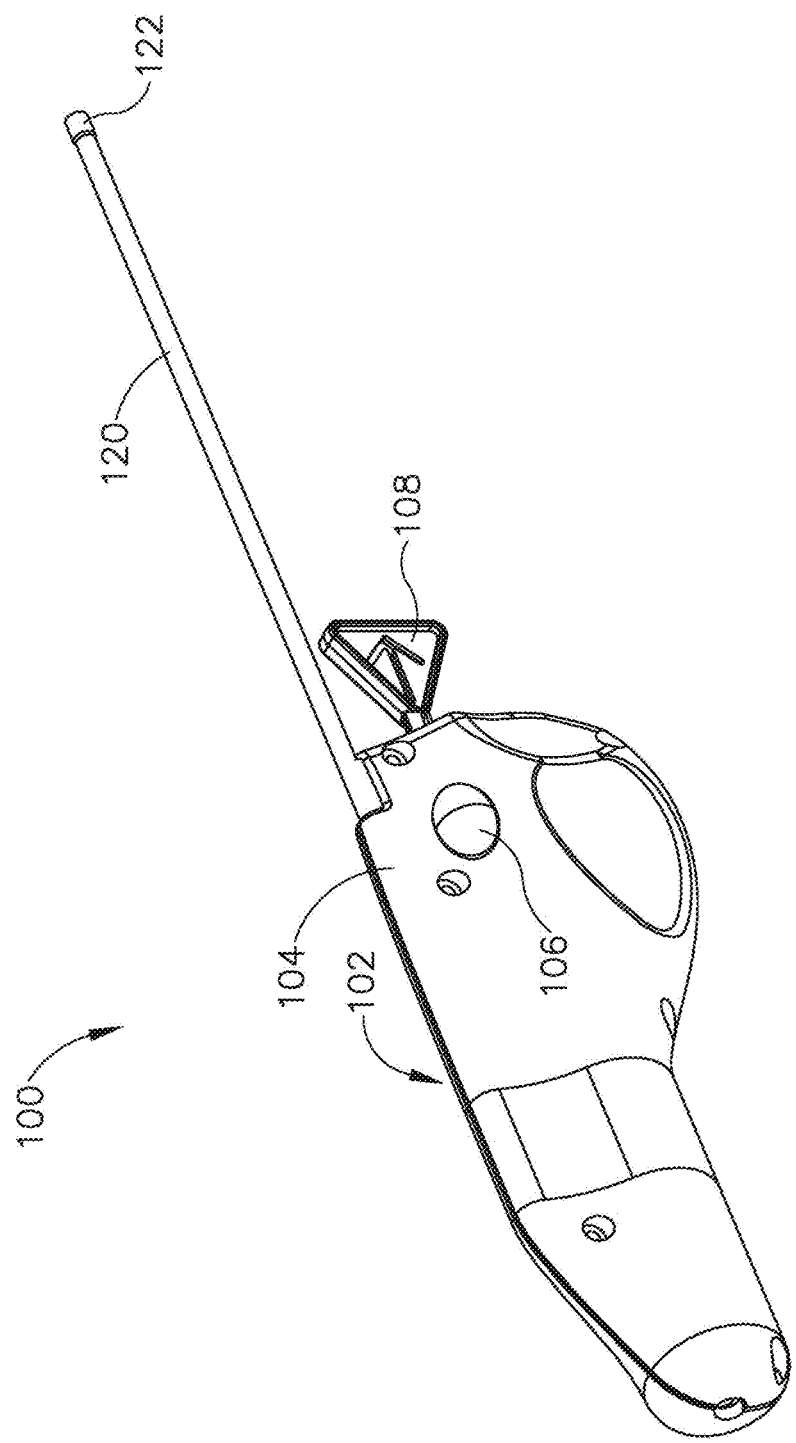
FIG. 1 depicts a perspective view of an exemplary pressure equalization tube delivery device (PETDD)

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc., described herein may be combined with any one or more of the other teachings, expressions, embodiments, examples, etc., that are described herein. The following-described teachings, expressions, embodiments, examples, etc., should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Pressure Equalization Tube Delivery Instrument

As noted above, a pressure equalization (PE) tube may be delivered to the tympanic membrane (TM) of a patient as a way of treating, for example, otitis media. In some instances, a delivery instrument may be used to insert PE tubes in the tympanic membrane (TM) without the use of general anesthesia. FIG. 1 shows an exemplary equalization tube delivery device (PETDD) (100) that may be used in such procedures. It should be understood that PETDD (100) may be used with an endoscope to provide visualization of the tympanic membrane (TM) during use of PETDD (100). It should also be understood that a patient may receive local anesthesia at the tympanic membrane (TM) through a process of iontophoresis before PETDD (100) is actuated to deploy a PE tube. By way of example only, such iontophoresis may be provided in accordance with at least some of the teachings of U.S. Pub. No. 2010/0198135, published Aug. 5, 2010, now U.S. Pat. No. 8,840,602, issued Sep. 23, 2014, the disclosure of which is incorporated by reference herein; and/or in accordance with at least some of the teachings of U.S. Pat. No. 8,192,420, the disclosure of which is incorporated by reference herein. Other suitable ways in which PETDD (100) may be used will be apparent to those of ordinary skill in the art in view of the teachings herein.

As shown in FIG. 1, PETDD (100) of this example comprises a handpiece (102) and a cannula (120) extending distally from handpiece (102). Handpiece (102) is formed by two housing (104) halves that are joined together and that include internal features configured to support various components of PETDD (100) as will be described below. Handpiece (102) is configured to be handheld, such that an operator may fully operate PETDD (100) using a single hand. A pushbutton (106) is slideably disposed in housing (104) and includes exposed portions extending laterally from each side of handpiece. Pushbutton (106) is operable to be pushed along a path that is transverse to handpiece (102) in order to actuate PETDD (100) as will be described in greater detail below. A pull-pin (108) extends distally from handpiece (102) and is configured to prevent pushbutton (106) from being actuated, thereby preventing PETDD (100) from being actuated, so long as pull-pin (108) is disposed in handpiece (102). Pull-pin (108) is nevertheless removable from handpiece (102) to effectively unlock pushbutton (106) and thereby enable actuation of PETDD (100). Cannula (120) of the present example comprises an elongate tube having a clear tip member (122) at the distal end of cannula (120). Clear tip member (122) is configured to contact a patient's tympanic membrane (TM) while enabling visualization of the distal end of cannula (120). In some versions, tip member (122) is formed of a soft or elastomeric material such as rubber, soft plastic, etc. This may dampen vibrations that might otherwise be transmitted from cannula (120) to the patient's tympanic membrane (TM) during firing of PETDD (100). In addition or in the alternative, tip member (122) may include some other kind of dampening feature as will be apparent to those of ordinary skill in the art in view of the teachings herein.

Figure 2:
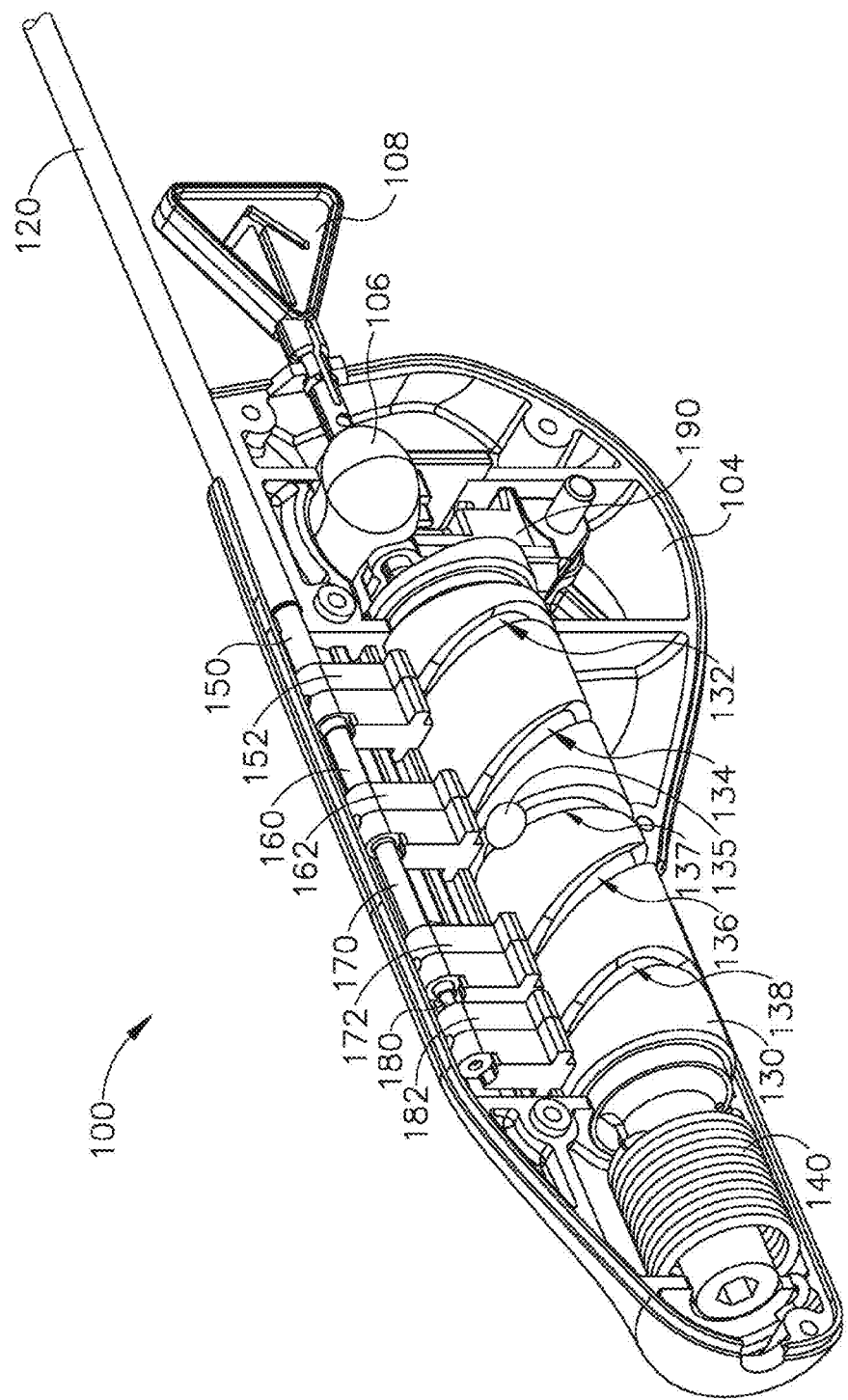
FIG. 2 depicts a perspective view of the PETDD of FIG. 1, with a housing half omitted.

As can be seen in FIG. 2, housing (104) supports a camshaft (130) and various other components. Camshaft (130) includes a dilator track (132), a shield tube track (134), a stopper track (137), a pusher track (136), and a piercer track (138). Tracks (132, 134, 136, 137, 138) are formed as recesses in camshaft (130) and each track (132, 134, 136, 137, 138) has a unique configuration in order to provide a particular sequence of operation of translating components as will be described in greater detail below. A torsion spring (140) is coupled to the proximal end of camshaft (130). Torsion spring (140) is also grounded against housing (104). Torsion spring (140) resiliently provides a rotational bias to camshaft (130). In particular, torsion spring (140) urges camshaft (130) to rotate in the clockwise direction (viewed from the distal end of PETDD (100) toward the proximal end of PETDD (100)) about the longitudinal axis of camshaft (130). As will be described in greater detail below (200), a trigger mechanism selectively resists such rotation. While torsion spring (140) is used to bias camshaft (130) in the present example, it should be understood that any other suitable types of components may be used to bias camshaft (130).

Figure 3:
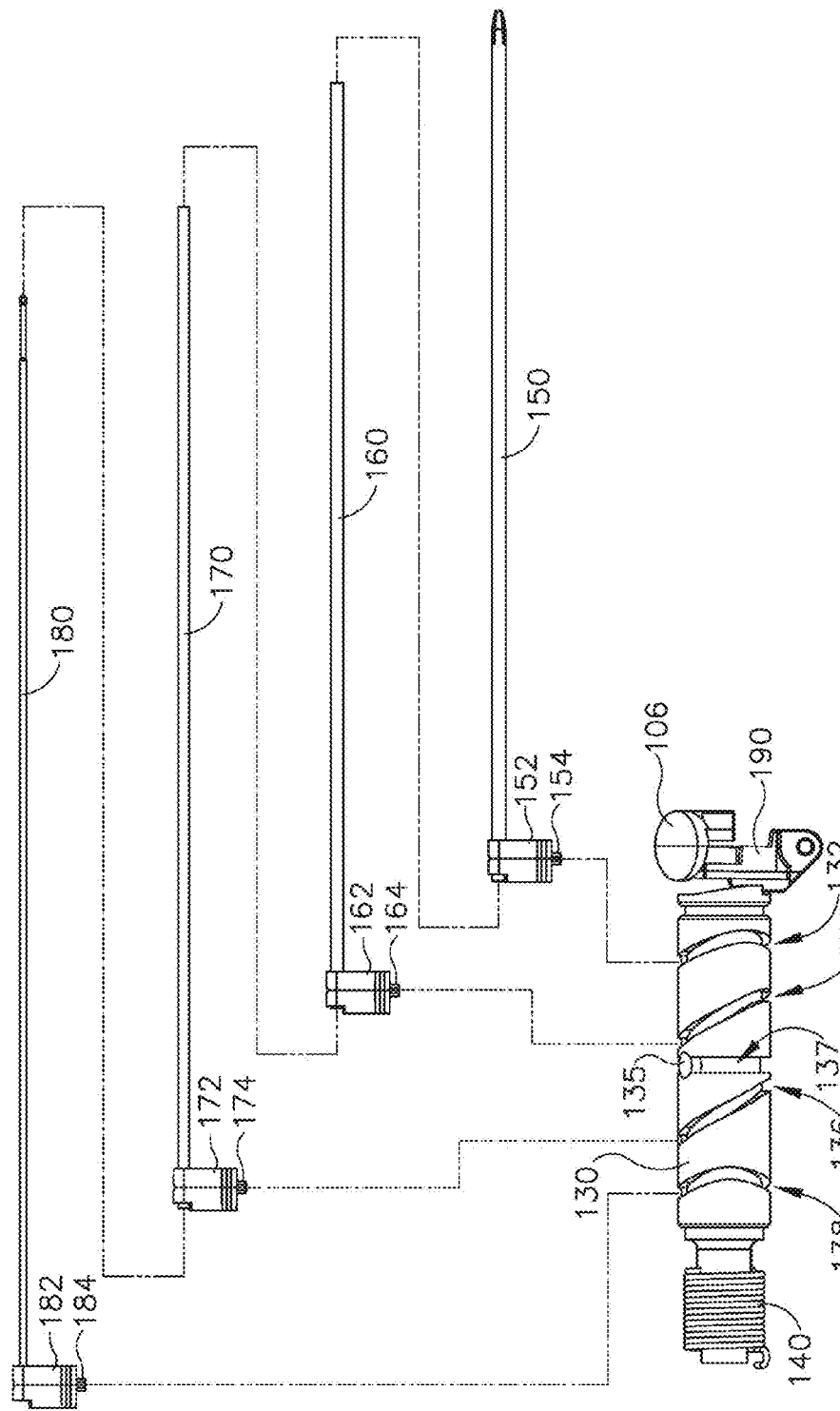
FIG. 3 depicts an exploded elevational view of actuation features of the PETDD of FIG. 1.

As shown in FIG. 3, various components are engaged with camshaft (130) and are thereby actuated by rotation of camshaft (130). In particular, a dilator tube (150), a shield tube (160), a pusher tube (170), and a piercer (180) are all engaged with camshaft (130). Tubes (150, 160, 170) and piercer (180) are all coaxially disposed within cannula (120). Piercer (180) is coaxially and slideably disposed within pusher tube (170), which is coaxially and slideably disposed within shield tube (160), which is coaxially and slideably disposed within dilator tube (150), which is coaxially and slideably disposed within cannula (120). Tubes (150, 160, 170) and piercer (180) all translate relative to cannula (120) in a particular sequence in order to deploy a PE tube as will be described in greater detail below. This sequence is driven by rotation of camshaft (130).

A cam follower (152) is fixedly secured to the proximal end of dilator tube (150). Cam follower (152) includes a laterally projecting pin (154) that is disposed in dilator track (132), such that rotation of camshaft (130) causes cam follower (152) and dilator tube (150) to translate. Similarly, a cam follower (162) is fixedly secured to the proximal end of shield tube (160). Cam follower (162) includes a laterally projecting pin (164) that is disposed in shield tube track (134), such that rotation of camshaft (130) causes cam follower (162) and shield tube (160) to translate. A cam follower (172) is fixedly secured to the proximal end of pusher tube (170). Cam follower (172) includes a laterally projecting pin (174) that is disposed in pusher tube track (136), such that rotation of camshaft (130) causes cam follower (172) and pusher tube (170) to translate. Finally, a cam follower (182) is fixedly secured to the proximal end of piercer (180). Cam follower (182) includes a laterally projecting pin (184) that is disposed in piercer track (138), such that rotation of camshaft (130) causes cam follower (182) and piercer (180) to translate. Stopper track (137) is simply annular in this example and includes a fixed elastomeric plug (135). An inwardly protruding boss (not shown) of housing (104) is disposed in stopper track (137). This boss remains disposed in stopper track (137) during rotation of camshaft (130).

Figure 4:
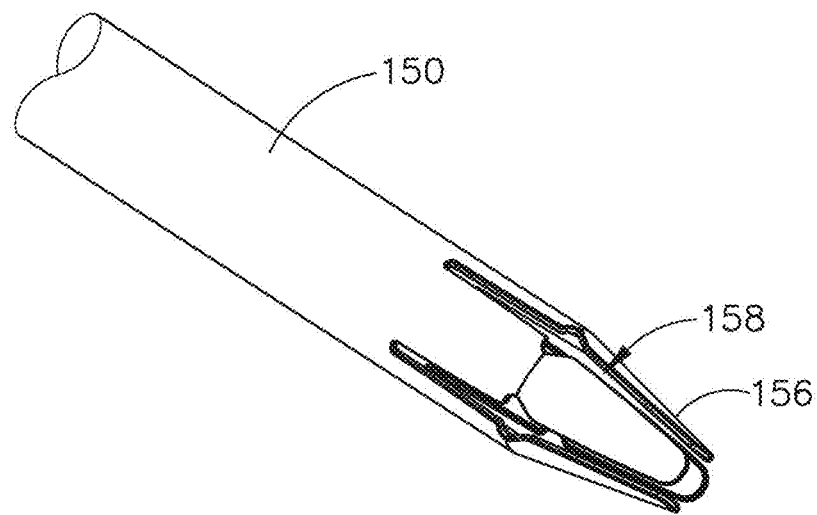
FIG. 4 depicts a perspective view of the distal end of a dilator of the actuation features of FIG. 3.
Figure 5:
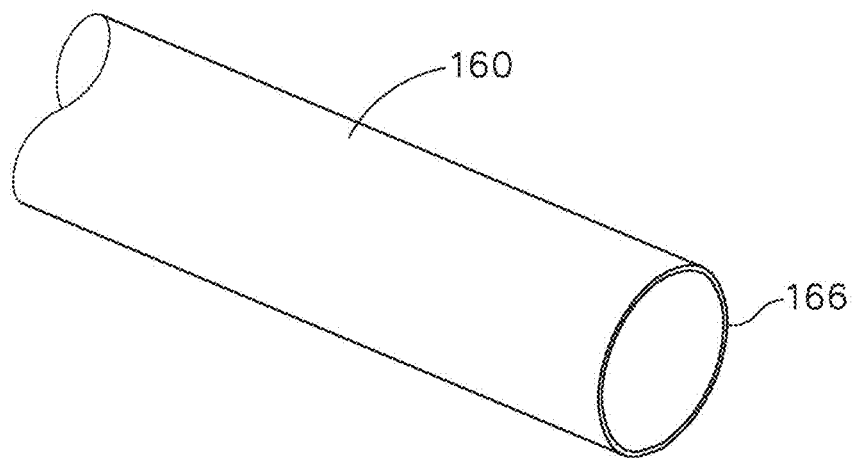
FIG. 5 depicts a perspective view of the distal end of a shield tube of the actuation features of FIG. 3.
Figure 6:
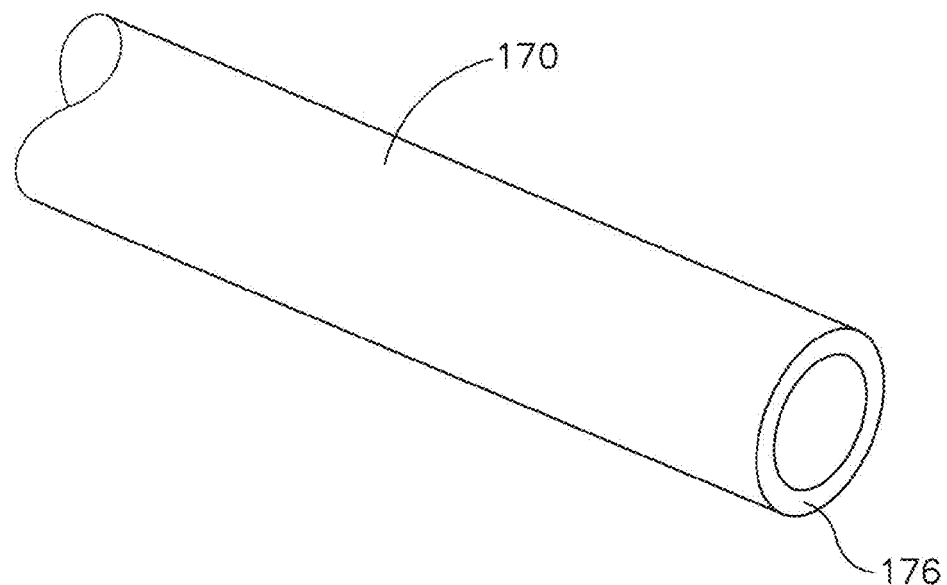
FIG. 6 depicts a perspective view of the distal end of a pusher of the actuation features of FIG. 3.
Figure 7:
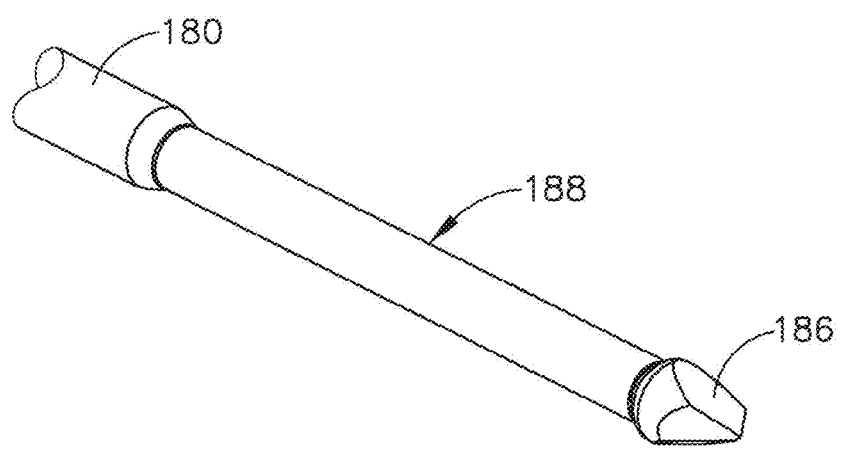
FIG. 7 depicts a perspective view of the distal end of a piercer of the actuation features of FIG. 3.

As shown in FIG. 4, the distal end of dilator tube (150) includes a plurality of generally flexible leaves (156) that are separated by longitudinally extending gaps (158). Leaves (156) are resiliently biased to assume the inwardly deflected positioning shown in FIG. 4; but are operable to flex outwardly from this positioning as will be described in greater detail below. As shown in FIG. 5, the distal end of shield tube (160) simply includes a circular edge (166). As shown in FIG. 6, the distal end of pusher tube (170) includes a distal face (176). In the present example, the difference between the inner diameter of pusher tube (170) and the outer diameter of pusher tube (170) is greater than the difference between the inner diameter of shield tube (160) and the outer diameter of shield tube (160). Thus, distal face (176) presents a more prominent contact surface than circular edge (166). As shown in FIG. 7, the distal end of piercer (180) includes a sharp, multi-faceted piercer tip (186) that is configured to pierce through a patient's tympanic membrane (TM). In the present example, piercer (180) also includes a neck-down region (188) having a reduced diameter.

Figure 8:
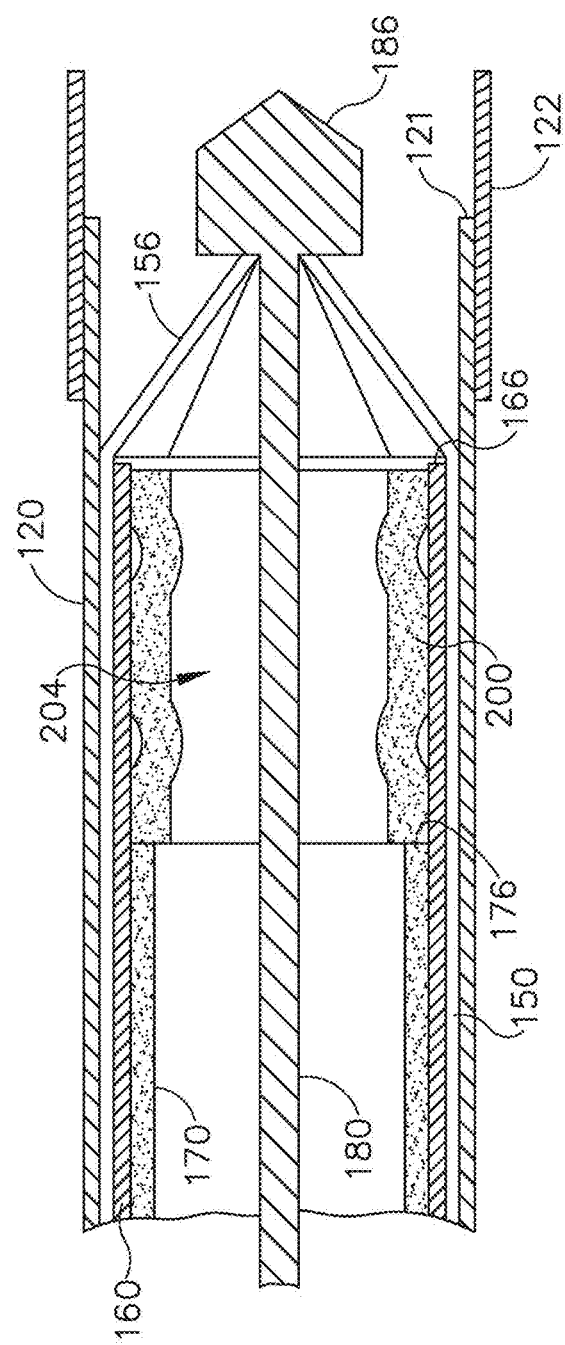
FIG. 8 depicts a cross-sectional side view of the actuation features of FIG. 3 with an exemplary pressure equalization (PE) tube.

FIG. 8 shows the positioning of tubes (150, 160, 170), piercer (180), and PE tube (200) within cannula (120) before camshaft (130) starts rotating from a home position. As shown, piercer tip (186) of piercer (180) is positioned distal to leaves (156) of dilator tube (150), such that leaves (156) are positioned about neck-down region (188) of piercer (180). PE tube (200) is positioned within the distal end of shield tube (160), whose distal edge (166) is just proximal to leaves (156). Pusher tube (170) is proximal to PE tube (200), with distal face (176) of pusher tube (170) abutting the proximal end of PE tube (200). In the present example, PE tube (200) is resiliently biased to assume a rivet-like shape presenting transverse petals (208) and a flange (206) (see FIG. 9). However, PE tube (200) is compressed against this bias, thereby assuming a generally cylindraceous configuration, when PE tube (200) is disposed within shield tube (160) as shown in FIG. 8.

Figure 9:
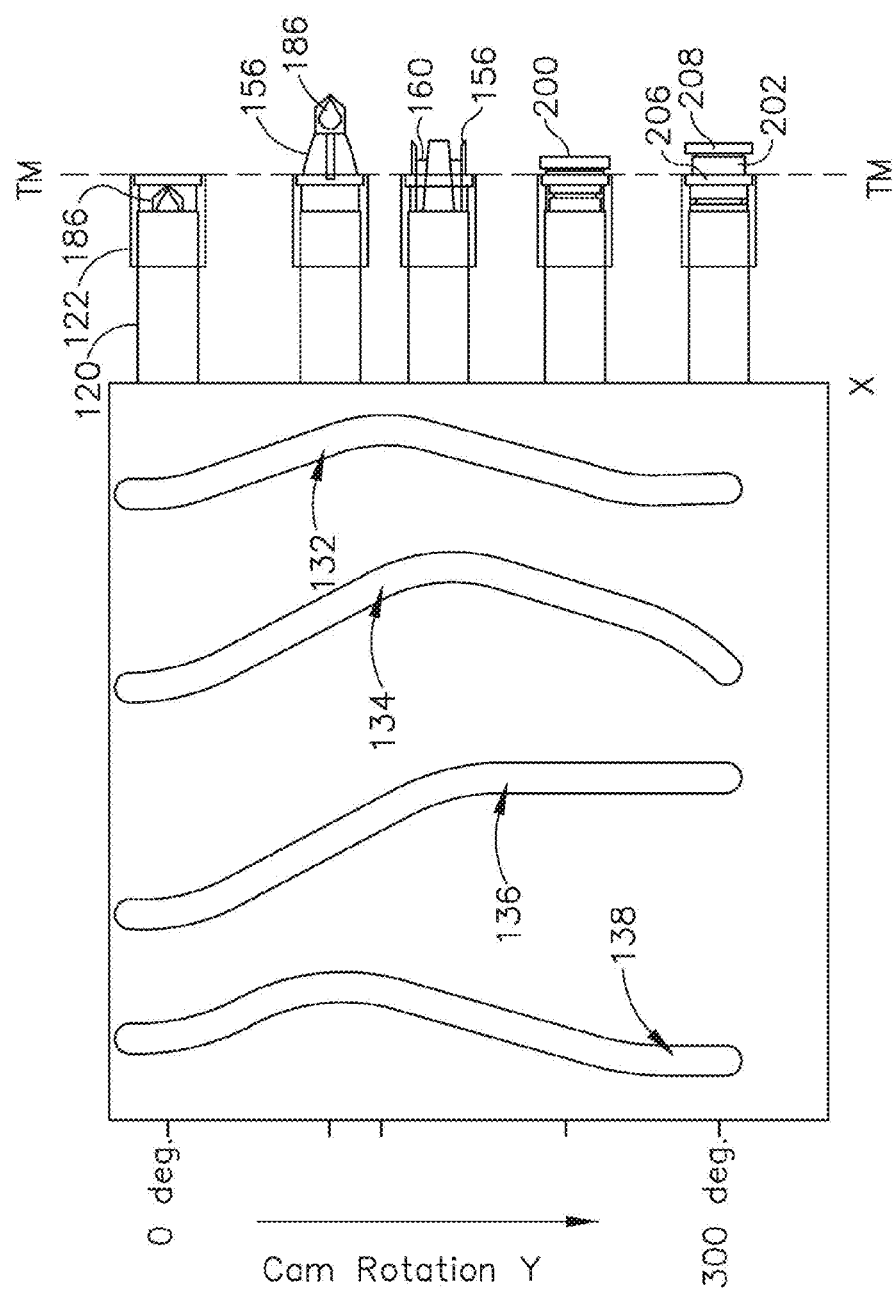
FIG. 9 depicts a displacement and operational diagram associated with the actuation features of FIG. 3.

FIG. 9 depicts a sequence of operation that occurs upon rotation of camshaft (130) from a home position to an actuated position, where tracks (132, 134, 136, 138) are shown developed into a flat pattern for purpose of illustration. The sequence starts at the top region of FIG. 9, which shows the distal end of clear tip member (122) contacting the patient's tympanic membrane (TM). At this stage, tubes (150, 160, 170), piercer (180), and PE tube (200) are at the positions shown in FIG. 8. Once camshaft (130) starts rotating at the urging of torsion spring (140), pins (154, 164, 174, 184) begin to ride along their respective tracks (132, 134, 136, 138), such that piercer tip (186) and leaves (156) are driven distally through the patient's tympanic membrane (TM). While not directly shown in FIG. 8, it should be understood that tubes (160, 170, 190) are also driven distally during this transition, though tubes (160, 170, 190) remain proximal to clear tip member (122) at this stage. As camshaft (130) continues to rotate, piercer (180) begins retracting proximally while tubes (160, 170, 190) continue to advance distally. As shown, shield tube (160) spreads leaves (156) outwardly from their default positions. This further dilates the puncture site in the tympanic membrane (TM). Shield tube (160) continues to contain PE tube (200) at this stage. As camshaft (130) continues to rotate, piercer (180) and dilator (150) retract proximally behind clear tip member (122). Shield tube (160) also begins to retract proximally, while pusher tube (170) remains longitudinally stationary. This relative movement uncovers the distal end of PE tube (200), such that the resilient bias of petals (208) causes petals (208) to flex to transverse positions, thereby effectively forming a flange on the far side of the tympanic membrane (TM). Piercer (180) eventually returns to the fully proximal position, dilator (170) eventually returns to the fully proximal position, and pusher tube (170) eventually reaches a fully distal position. As camshaft (130) continues to rotate, shield tube (160) continues to retract proximally while pusher tube (170) remains longitudinally stationary. This relative movement uncovers the proximal end of PE tube (200), such that the resilient bias of PE tube (200) is allowed to form flange (206) on the near side of the tympanic membrane (TM).

[Camshaft (130) stops rotating when the inwardly protruding boss of housing (104) engages plug (135) in stopper track (137). The elastomeric nature of plug (135) provides a relatively soft stop, such that plug (135) acts as a damper. This may reduce jolting of PETDD (100) when camshaft (130) comes to a stop and/or may prevent camshaft (130) from making a popping or snapping sound when camshaft (130) comes to a stop. Upon completion of the above described sequence shown in FIG. 9, cannula (120) is withdrawn from the patient's ear, leaving the actuated PE tube (200) in place in the patient's tympanic membrane (TM). Petals (208) and flange (206) cooperate to maintain the position of PE tube (200) in TM, while the passageway (204) formed by the interior of PE tube (200) (see FIGS. 8 and 17-20) provides a path for fluid communication (e.g., venting) between the patient's middle ear and outer ear. This fluid path further provides pressure equalization between the patient's middle ear and outer ear and/or promotes drainage of fluid from the middle ear via the Eustachian tube.

As noted above, PETDD (100) of the present example includes a trigger mechanism that is configured to selectively resist rotation of camshaft (130) by torsion spring (140). As best seen in FIGS. 10-16B, the trigger mechanism of this example comprises a pawl member (190) that selectively engages pushbutton (106) and camshaft (130). Pawl member (190) includes laterally extending pins (192) that couple pawl member (190) with housing (104). While housing (104) prevents pawl member (190) from moving laterally within housing (104), housing (104) permits pawl member (190) to pivot freely about pins (192) within housing (104). Pawl member (190) includes a distally facing boss rib (194) that extends vertically. Pawl member (190) also includes a pull-pin opening (196) and a proximally facing pawl ridge (198). Boss rib (194) is configured to selectively engage a proximally facing boss rib (107) of pushbutton (106) as will be described in greater detail below. Pull-pin opening (196) is configured to receive pull-pin (108), which assists to prevent pawl member (190) from pivoting about pins (192) when pull-pin (108) is disposed in pull-pin opening (196). Pawl ridge (198) includes chamfered lateral faces (199) and is configured to selectively engage a retention feature (131) of camshaft (130). In particular, when pawl member (190) is in a first position as shown in FIGS. 14, 15A, and 16A, pawl ridge (198) is engaged with retention feature (131) and prevents camshaft (130) from rotating despite the rotational bias provided by torsion spring (140). When pawl member (190) is pivoted to a second position as shown in FIGS. 15B and 16B, pawl ridge (198) disengages retention feature (131), enabling camshaft (130) to rotate under the influence of torsion spring (140) to provide the sequence of operation described above.

Figure 10:
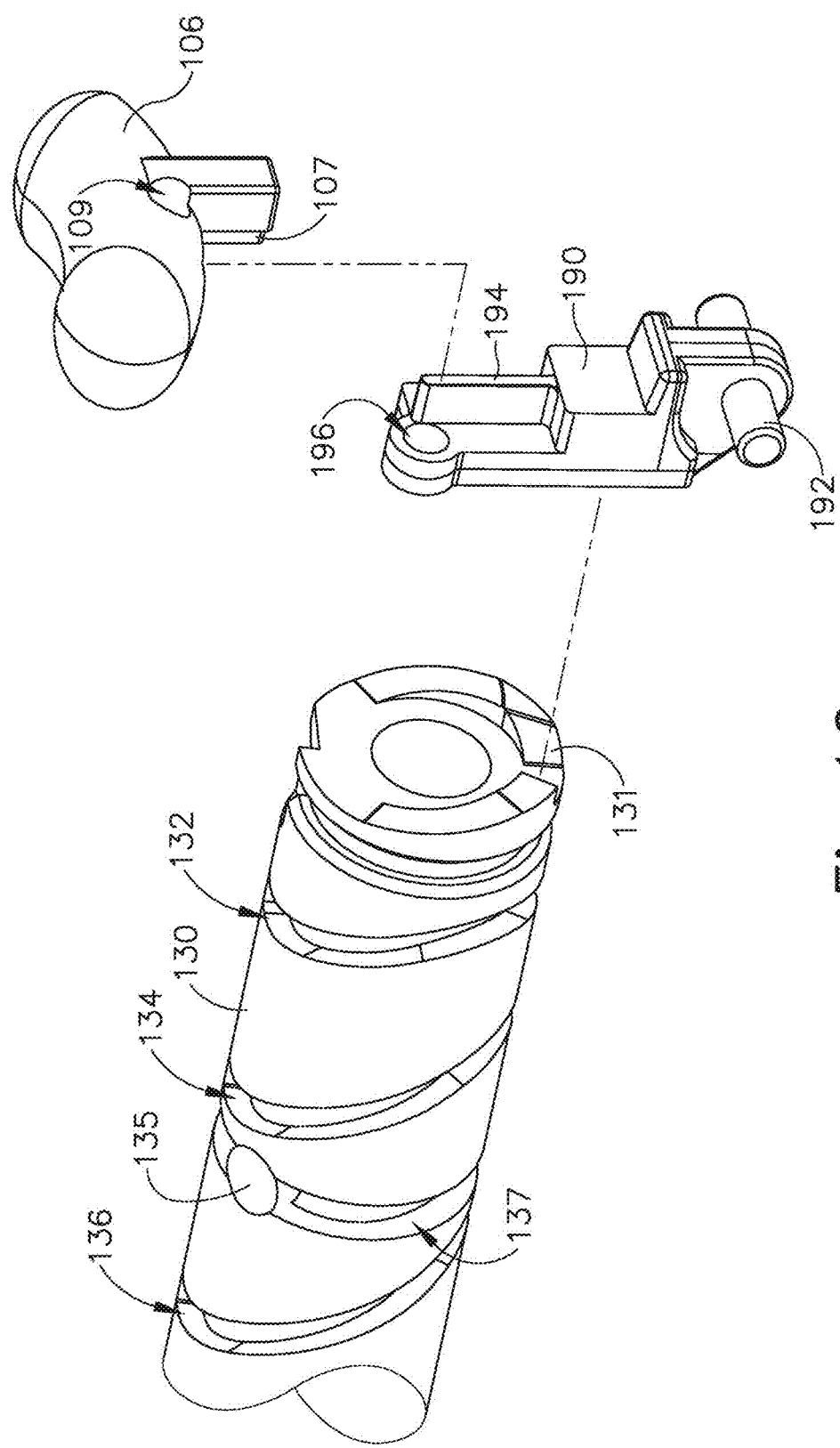
FIG. 10 depicts an exploded perspective view of a trigger mechanism of the actuation features of FIG. 3.
Figure 12:
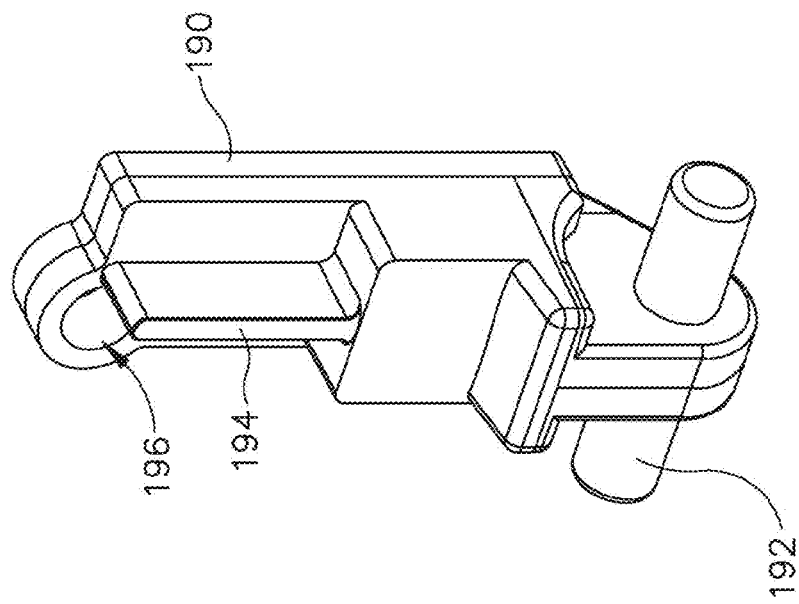
FIG. 12 depicts a perspective view of the distal side of the pawl of FIG. 11.
Figure 11:
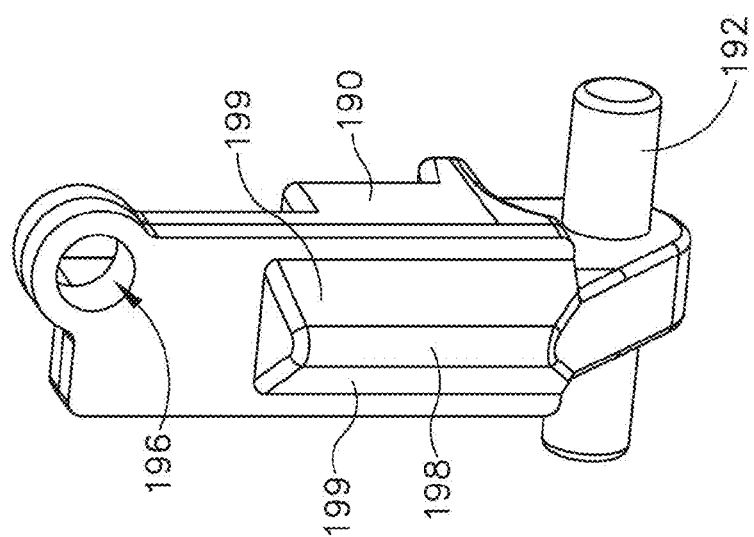
FIG. 11 depicts a perspective view of the proximal side of a pawl of the trigger mechanism of FIG. 10.
Figure 13:
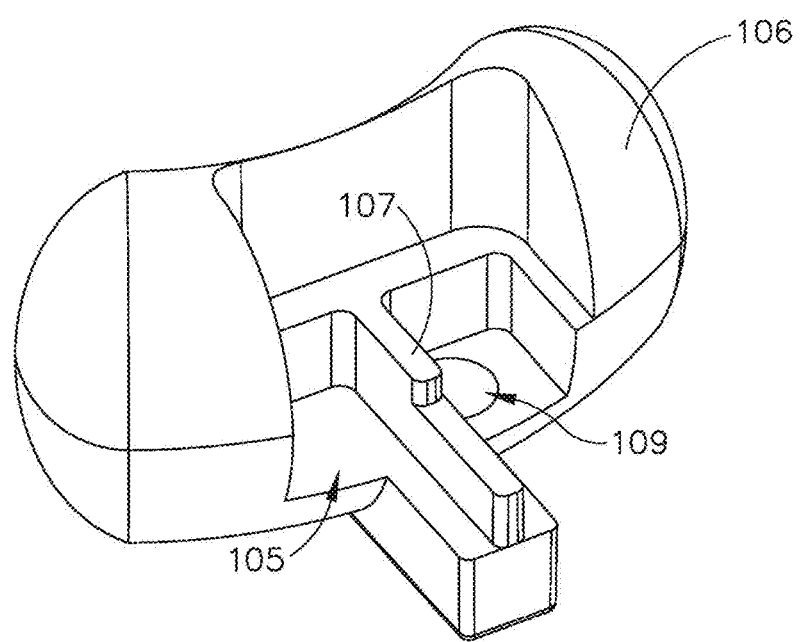
FIG. 13 depicts a perspective view of the proximal underside of a button actuator of the trigger mechanism of FIG. 10.
Figure 17:
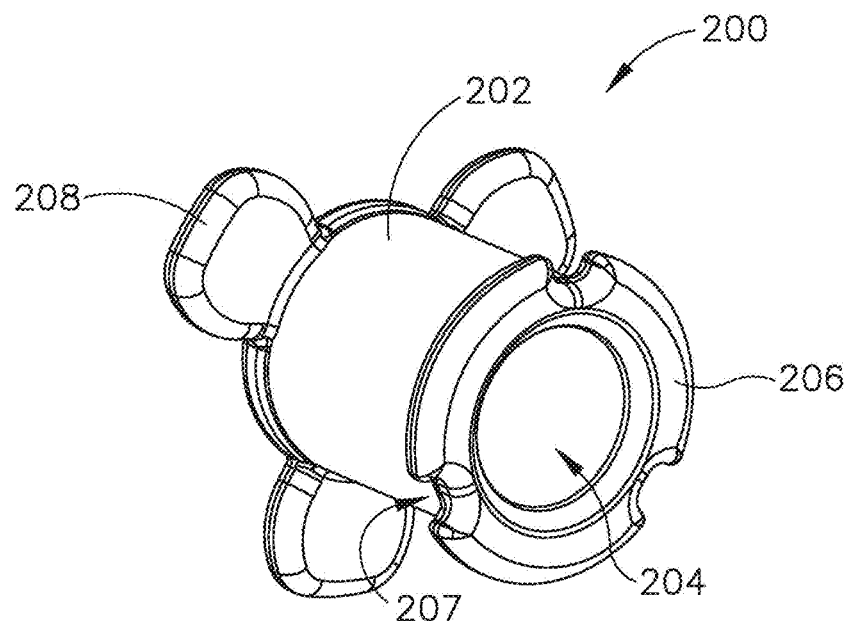
FIG. 17 depicts a perspective view of the proximal side of an exemplary PE tube suitable for delivery by the PETDD of FIG. 1.
Figure 18:
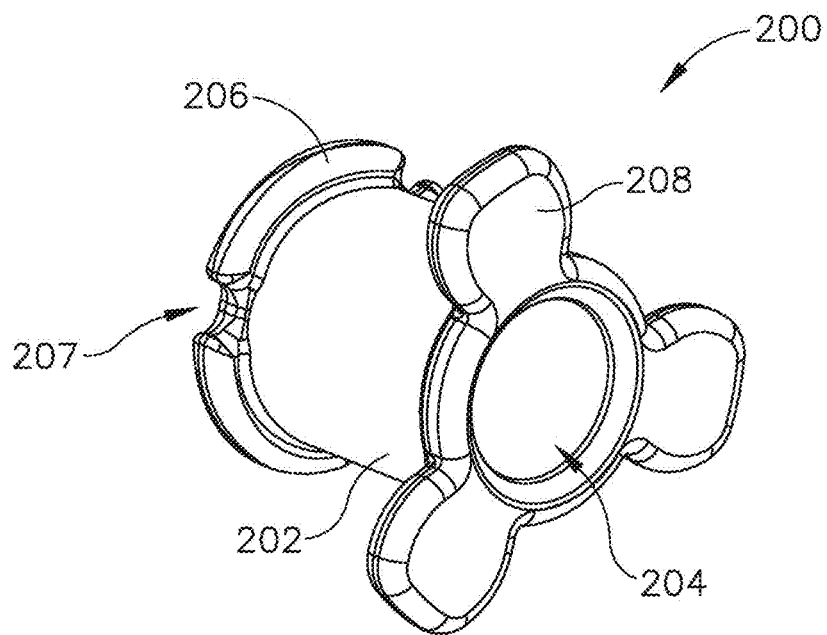
FIG. 18 depicts a perspective view of the distal side of the PE tube of FIG. 17.
Figure 19:
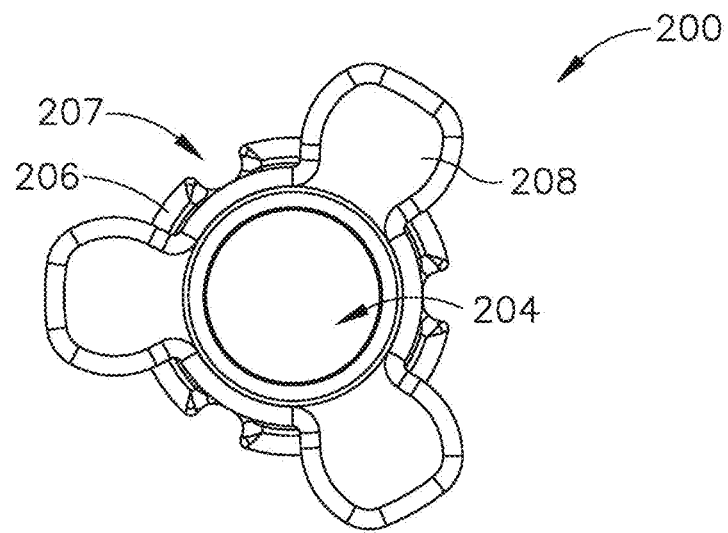
FIG. 19 depicts a distal elevational view of the PE tube of FIG. 17.
Figure 20:
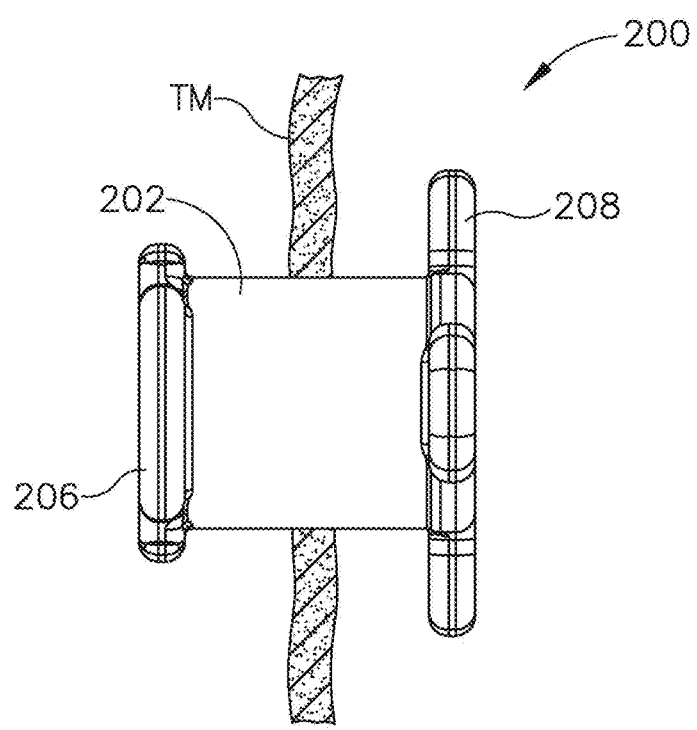
FIG. 20 depicts a side elevational view of the PE tube of FIG. 17, positioned within a tympanic membrane.

As best seen in FIGS. 10 and 13, pushbutton (106) includes a pull-pin opening (109) that is configured to receive pull-pin (108). Pushbutton (106) is prevented from translating laterally relative to housing (104) when pull-pin (108) is disposed within pull-pin opening (109). Pull-pin (108) thus provides a lockout for pushbutton (106). To unlock pushbutton (106), pull-pin (108) may be pulled distally out of housing (104). As noted above, pushbutton (106) also includes a proximally facing boss rib (107) that extends vertically. When pushbutton (106) is laterally centered within housing (104), boss rib (107) engages boss rib (194), as shown in FIGS. 15A and 16A. This engagement prevents pawl member (190) from pivoting distally about pins (192). Pushbutton (106) and pawl member (190) together thus effectively lock camshaft (130) when pushbutton (106) is laterally centered within housing (104).

When pushbutton (106) is laterally displaced relative to housing (104) (i.e., when a user depresses an exposed portion of pushbutton (106) laterally relative to housing (104)), bosses (107, 194) disengage such that pushbutton (106) no longer blocks pivoting of pawl member (190). Due to the torsional bias of camshaft (130), the ramped configuration of retention feature (131), and the chamfered lateral faces (199) of pawl ridge (198), camshaft (130) forces pawl member (190) to pivot out of the way to the position shown in FIGS. 15B and 16B when pushbutton (106) is no longer blocking pawl member (190). This enables camshaft (130) to complete the operational drive sequence described above. While pushbutton (106) is depicted as being pushed in one lateral direction, it should be understood that the same triggering operation may be provided when pushbutton (106) is pushed in the opposite lateral direction from the center position. With portions of pushbutton (106) being exposed through housing (104) on each side of handpiece (102), this allows the operator to select which side of pushbutton (106) to press.

It should be understood that the foregoing components, features, and operabilities of PETDD (100) are merely illustrative examples. A PETDD (100) may include various other features in addition to or in lieu of those described above. By way of example only, any of the devices herein may also include one or more of the various features disclosed in any of the various references that are incorporated by reference herein. Some additional merely illustrative variations of PETDD (100) will be described in greater detail below, while other variations of PETDD (100) will be apparent to those of ordinary skill in the art in view of the teachings herein.

II. Exemplary Pressure Equalization Tube

FIGS. 17-20 show PE tube (200) in greater detail. PE tube (200) of this example includes a cylindraceous body (202) that defines a passageway (204). A flange (206) is located at the proximal end of body (202) while a set of petals (208) are located at the distal end of body (202). Flange (206) includes a plurality of inwardly directed recesses (207). Recesses (207) are configured to facilitate flexing of flange (206) from an outwardly extended position to a generally cylindraceous position where the material forming flange (206) extends longitudinally. While three recesses (207) are shown, it should be understood that any other suitable number of recesses (207) may be provided. Similarly, while three petals (208) are shown, it should be understood that any other suitable number of petals (208) may be provided.

PE tube (200) is formed of a resilient material that is biased to assume the rivet like configuration shown in FIGS. 17-20. However, flange (206) and petals (208) may be flexed inwardly toward the longitudinal axis of body (202) to provide PE tube (200) with a cylindraceous configuration. In particular, flange (206) and petals (208) may be flexed such that their outer surfaces are at the same radial distance from the longitudinal axis as the outer perimeter of body (202). This radial distance may be slightly less than the radial distance associated with the inner diameter of shield tube (160), such that PE tube (200) may collapse to fit within shield tube (160). When PE tube (200) is disposed in a tympanic membrane (TM), petals (208) are located medially (i.e., on the middle ear side) while flange (206) is located laterally (i.e., on the outer ear side). By way of example only, PE tube (200) may also be configured in accordance with at least some of the teachings of U.S. patent application Ser.

No. 13/800,113, entitled "Tympanic Membrane Pressure Equalization Tube," filed on Mar. 13, 2013, now U.S. Pat. No. 9,011,363, issued Apr. 21, 2015, the disclosure of which is incorporated by reference herein. Other suitable forms that PE tube (200) may take will be apparent to those of ordinary skill in the art in view of the teachings herein.

III. Exemplary Pressure Equalization Tube Delivery Instrument Variations

Those of ordinary skill in the art will appreciate that the tympanic membrane (TM) may extend along a plane that is oblique to the direction of insertion of PETDD (100). In other words, the plane of the tympanic membrane (TM) may be obliquely angled relative to the longitudinal axis of cannula (120). By way of example only, the tympanic membrane (TM) may define an angle between approximately 79 degrees and approximately 54 degrees with the longitudinal axis of cannula (120). This oblique orientation of the tympanic membrane (TM) may pose difficulties with respect to some versions of a PETDD (100) that has a flat tip. For instance, inadequate apposition between the distal edge of tip member (122) and the tympanic membrane (TM) may lead to unsuccessful deployment of PE tube (200). This may prompt some operators of PETDD (100) to apply significant pressure against the tympanic membrane (TM), to deform the tympanic membrane (TM) into a position of substantial apposition with the flat-faced tip member (122) of PETDD (100). It may be desirable to maximize the apposition between the distal edge of tip member (122) and the tympanic membrane (TM), such as by enabling the distal edge of tip member (122) to complement the orientation of the tympanic membrane (TM) as much as possible, without requiring an operator to apply significant pressure against the tympanic membrane (TM) in order to achieve adequate apposition. The following examples include merely illustrative variations of PETDD (100) that may enhance apposition with the tympanic membrane (TM).

A. Exemplary PETDD with Tip Sleeve Having Complementary Bevel

Figure 21:
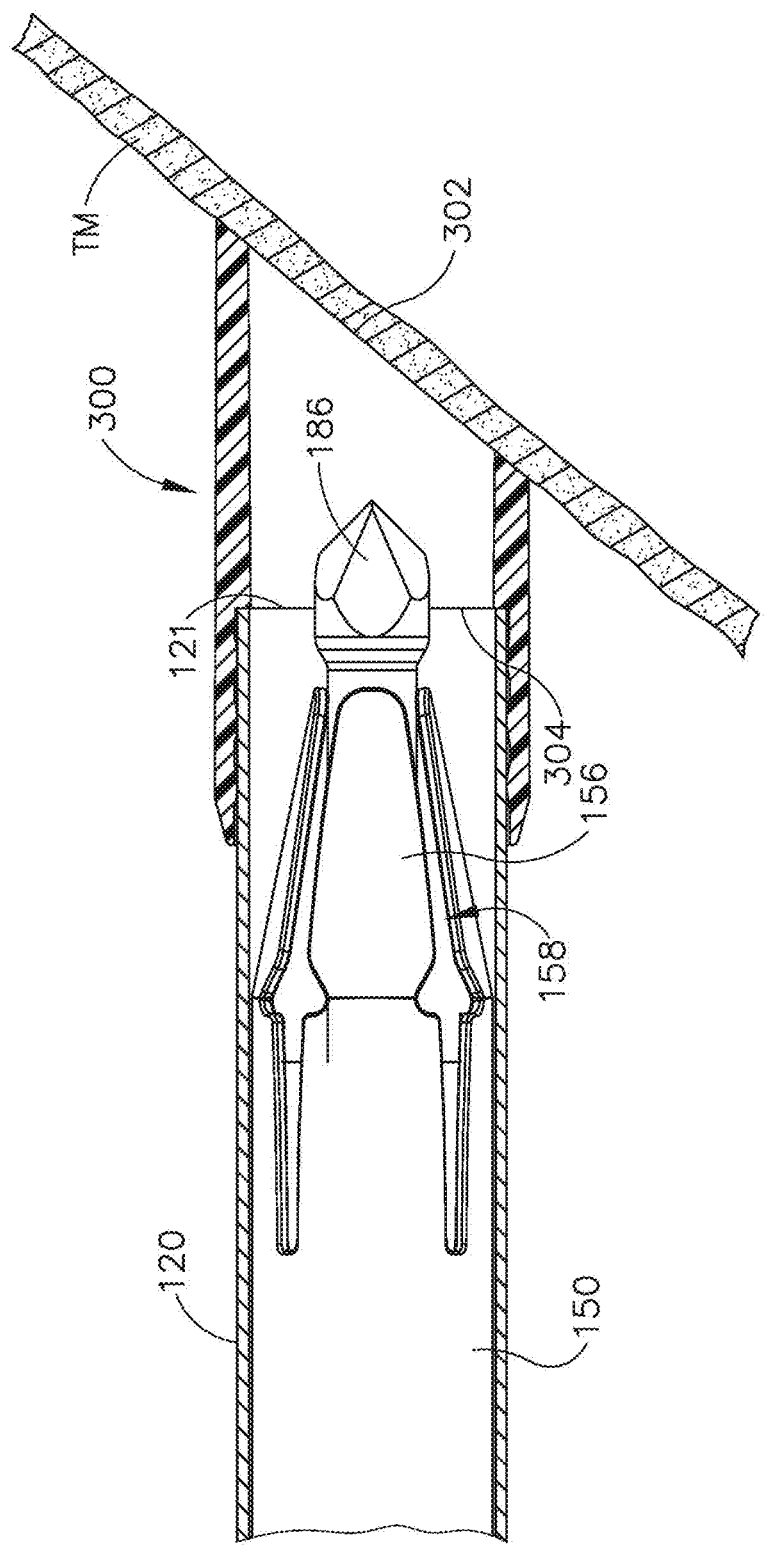
FIG. 21 depicts a side elevational view of a PETDD cannula having an exemplary alternative tip member, with the outer tube and tip member shown in cross-section, engaged with a tympanic membrane.

FIG. 21 depicts an exemplary variation of PETDD (100) having a beveled tip member (300) secured to the distal end of cannula (100). All of the other components in this variation are the same as those described above for PETDD (100). As can be seen, the distal edge (121) of cannula (120) extends along a plane that is perpendicular to the longitudinal axis of cannula (120). Beveled tip member (300) is secured to the distal end of cannula (120). Beveled tip member (300) includes an interior annular shoulder (304), such that cannula (120) is inserted into the proximal end of beveled tip member (300) until distal edge (121) of cannula (120) engages annular shoulder (304). An adhesive, interference fit, and/or any other suitable structure/technique may be used to secure beveled tip member (300) to the distal end of cannula (120). Beveled tip member (300) and cannula (120) are both configured to be inserted through the ear canal of the patient to reach the tympanic membrane (TM). In the present example, beveled tip member (300) is formed of a transparent material, which may facilitate visualization with an endoscope or other visualization apparatus. In versions where beveled tip member (300) is transparent, the distal edge (302) of beveled tip member (300) may nevertheless be opaque or colored, to assist in visualizing the positioning of distal edge (302) against the tympanic membrane (TM).

Distal edge (302) of beveled tip member (300) is formed at an oblique angle in the present example. By way of example only, distal edge (302) may extend along a plane that defines an angle between approximately 79 degrees and approximately 54 degrees with the longitudinal axis of cannula (120). In other words, distal edge (302) may be oriented at an angle between about 11 degrees and about 36 degrees relative to the plane along which distal edge (303) of cannula (120) extends. Alternatively, any other suitable angles may be used. In the present example, the orientation of distal edge (302) may substantially complement the orientation of the tympanic membrane (TM). Accordingly, when beveled tip member (300) is positioned adjacent to the tympanic membrane (TM) as shown in FIG. 21, distal edge (302) may achieve substantial apposition with the tympanic membrane (TM) without the operator of PETDD (300) having to apply significant pressure against the tympanic membrane (TM).

In an exemplary use, an operator may first anesthetize the patient's ear using an iontophoresis system as described in various references cited herein. Once the ear has been suitably anesthetized, the operator may remove pull-pin (108) from handpiece (102) by pulling distally on pull-pin (108) until pull-pin (108) is fully separated from housing (104). This will effectively unlock pushbutton (106) and enable operation of PETDD (100). The operator may then insert cannula (120) into a patient's ear canal. With the aid of a visualization system such as a scope, the operator may position distal edge (302) of beveled tip member (300) against the tympanic membrane (TM). This may require the operator to rotate PETDD (100) about the longitudinal axis of cannula (120) in order to orient distal edge (302) parallel with the tympanic membrane (TM). In some versions of PETDD (100), cannula (120) is rotatable relative to handpiece (102), such that the user may readily rotate cannula (120) about the longitudinal axis of cannula (120) while holding handpiece (120) stationary.

Once distal edge (302) has been oriented to be substantially parallel with the tympanic membrane (TM), and distal edge (302) is in apposition with the tympanic membrane (TM), the operator may press pushbutton (106) laterally to fire PETDD (100) and thereby deploy a PE tube (200) in the tympanic membrane (TM). It should be understood that the complementary orientations of distal edge (302) and the tympanic membrane (TM) may reduce the chances that PE tube (200) might fail to properly enter the dilated incision in the tympanic membrane (TM) during deployment. Once PE tube (200) is positioned within the tympanic membrane (TM), PETDD (100) may be retracted proximally and PE tube (200) may remain in the tympanic membrane (TM) in the rivet-like configuration shown in FIGS. 17-20.

B. Exemplary PETDD with Tip Having Opposing Bevel

Figure 22A:
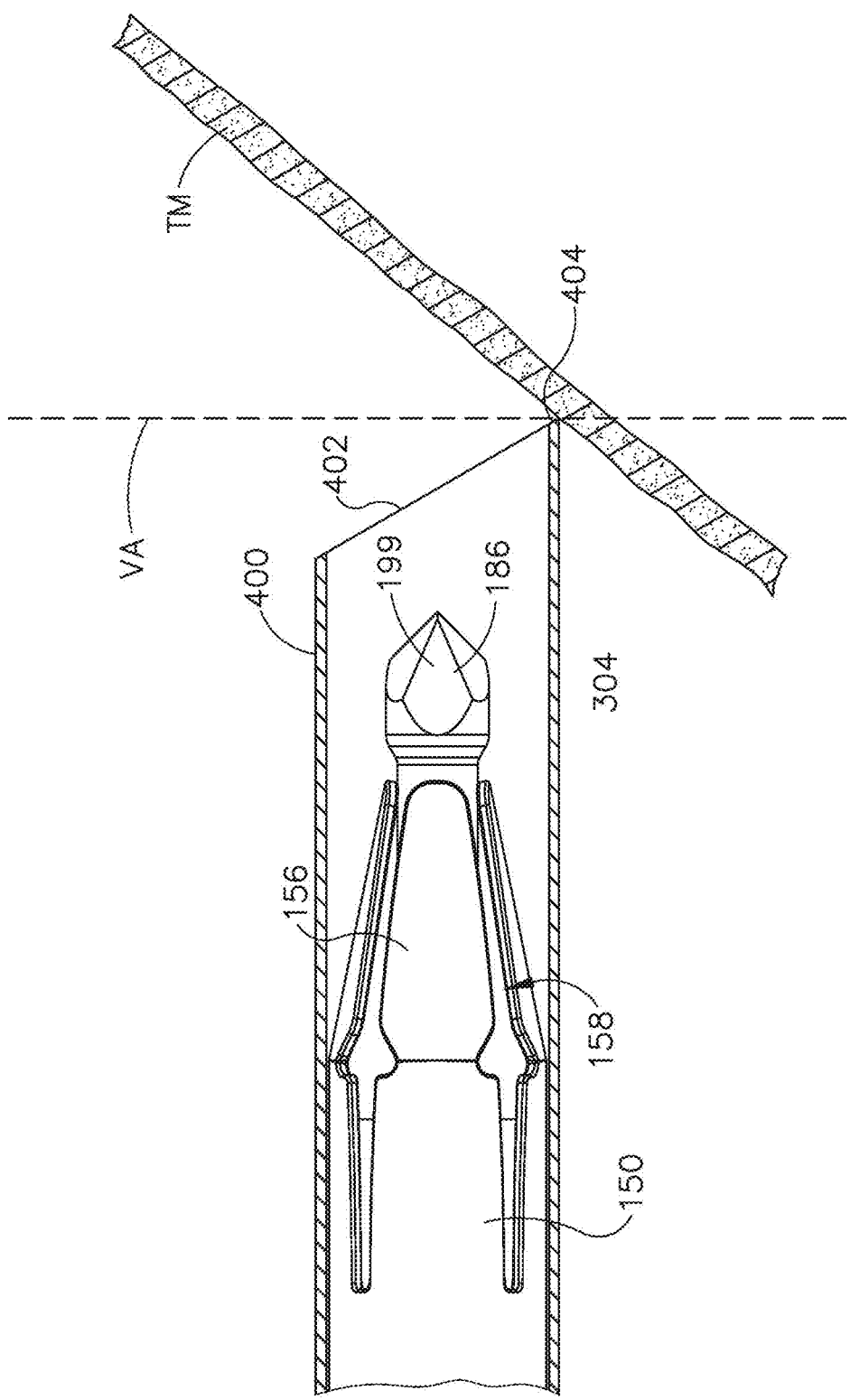
FIG. 22A depicts a side elevational view of a an exemplary alternative PETDD cannula, with the cannula shown in cross-section, engaged with a tympanic membrane.
Figure 22B:
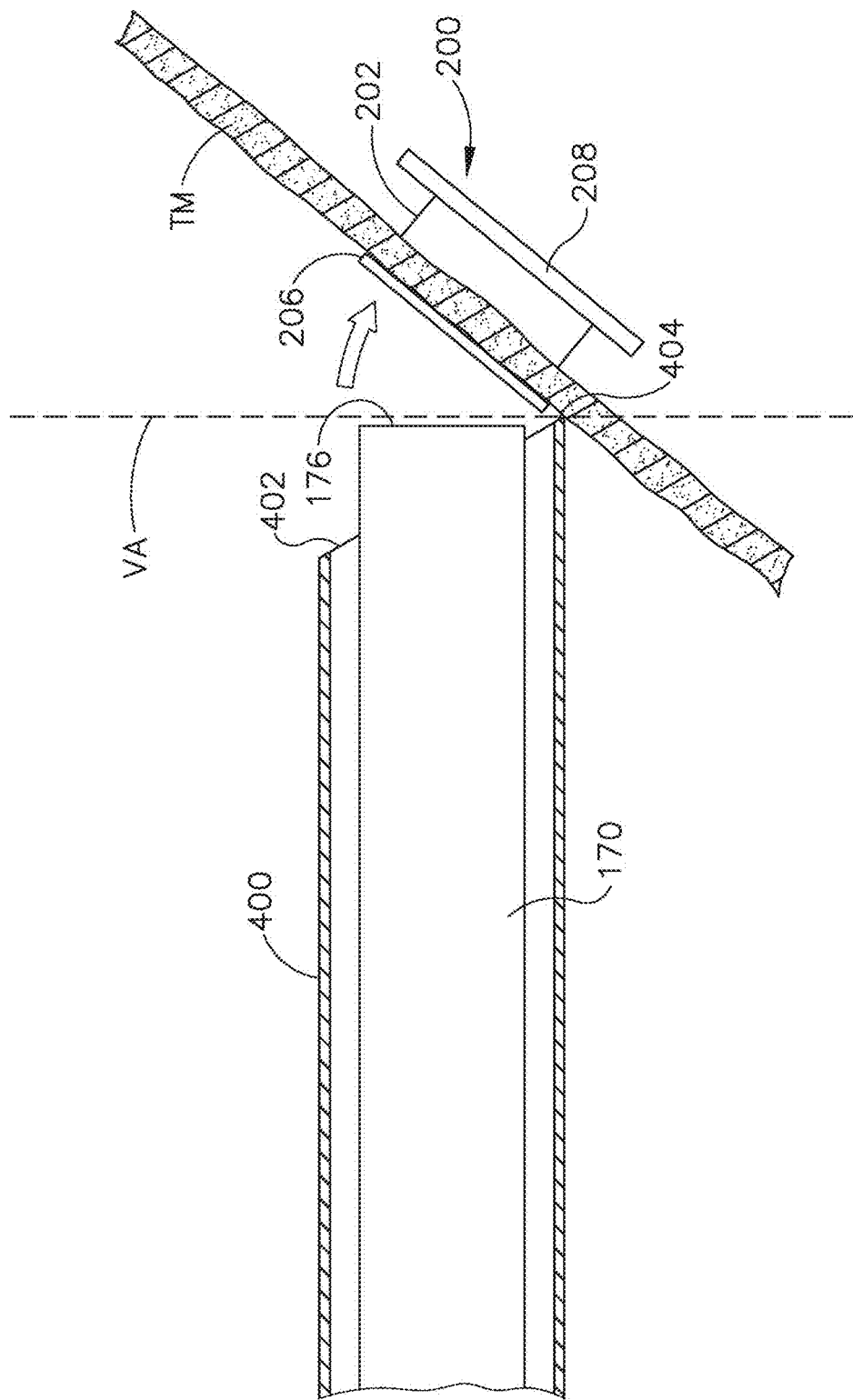
FIG. 22B depicts a side elevational view of the PETDD cannula of FIG. 22A, having delivered a PE tube in the tympanic membrane.

FIGS. 22A-22B depict an exemplary variation of PETDD (100) having a cannula (400) with a beveled distal edge (402). All of the other components in this variation are the same as those described above for PETDD (100). As can be seen, the distal edge (402) of cannula (400) extends along a plane that defines an angle between approximately 79 degrees and approximately 54 degrees with the longitudinal axis of cannula (400). Alternatively, any other suitable angles may be used.

In an exemplary use, an operator may first anesthetize the patient's ear using an iontophoresis system as described in various references cited herein. Once the ear has been suitably anesthetized, the operator may remove pull-pin (108) from handpiece (102) by pulling distally on pull-pin (108) until pull-pin (108) is fully separated from housing (104). This will effectively unlock pushbutton (106) and enable operation of PETDD (100). The operator may then insert cannula (400) into a patient's ear canal. With the aid of a visualization system such as a scope, the operator may position the distal-most portion (404) of distal edge (402)

adjacent the tympanic membrane (TM). However, instead of placing distal edge (402) in apposition with the tympanic membrane (TM), PETDD (100) is oriented such that distal edge (402) forms a vertically opposing angle with the tympanic membrane (TM). In particular, distal edge (402) forms an angle with a vertical axis (VA) that is approximately the same as the angle formed between the tympanic membrane (TM) and the vertical axis (VA), with those angles being located on opposite sides of the vertical axis (VA). By way of example only, these angles may be between approximately 11 degrees and approximately 36 degrees. In some instances, the user may rotate PETDD (100) about the longitudinal axis of cannula (400) in order to achieve this positioning. In some versions of PETDD (100), cannula (400) is rotatable relative to handpiece (102), such that the user may readily rotate cannula (400) about the longitudinal axis of cannula (400) while holding handpiece (120) stationary.

Once PETDD (100) is oriented such that distal edge (402) forms a vertically opposing angle with the tympanic membrane (TM), the operator may press pushbutton (106) laterally to fire PETDD (100) and thereby deploy a PE tube (200) in the tympanic membrane (TM). It should be understood that the angularly opposing orientations of distal edge (402) and the tympanic membrane (TM) may promote PE tube (200) pivoting into the position shown in FIG. 22B as PE tube (200) is being deployed into the tympanic membrane (TM). This pivoting of PE tube (200) may reduce the risk of PE tube (200) being undesirably displaced laterally or medially during deployment of PE tube (406). As can also be seen in FIG. 22B, a portion of pusher tube (170) may protrude slightly from the open distal end of cannula (120) during deployment of PE tube (200). (Other features inside cannula (120) are omitted from the view in FIG. 22B for clarity). Once PE tube (200) is positioned within the tympanic membrane (TM), PETDD (100) may be retracted proximally and PE tube (200) may remain in the tympanic membrane (TM) in the rivet-like configuration shown in FIGS. 17-20. It should be understood that the deployment technique shown in FIGS. 22A-22B may also be performed with a PETDD (100) that has a beveled tip member (300) like the one shown in FIG. 21, simply by rotating cannula (120) about its longitudinal axis by approximately 180 degrees.

C. Exemplary PETDD with Driven Apposition Enhancement Features

Figure 23:
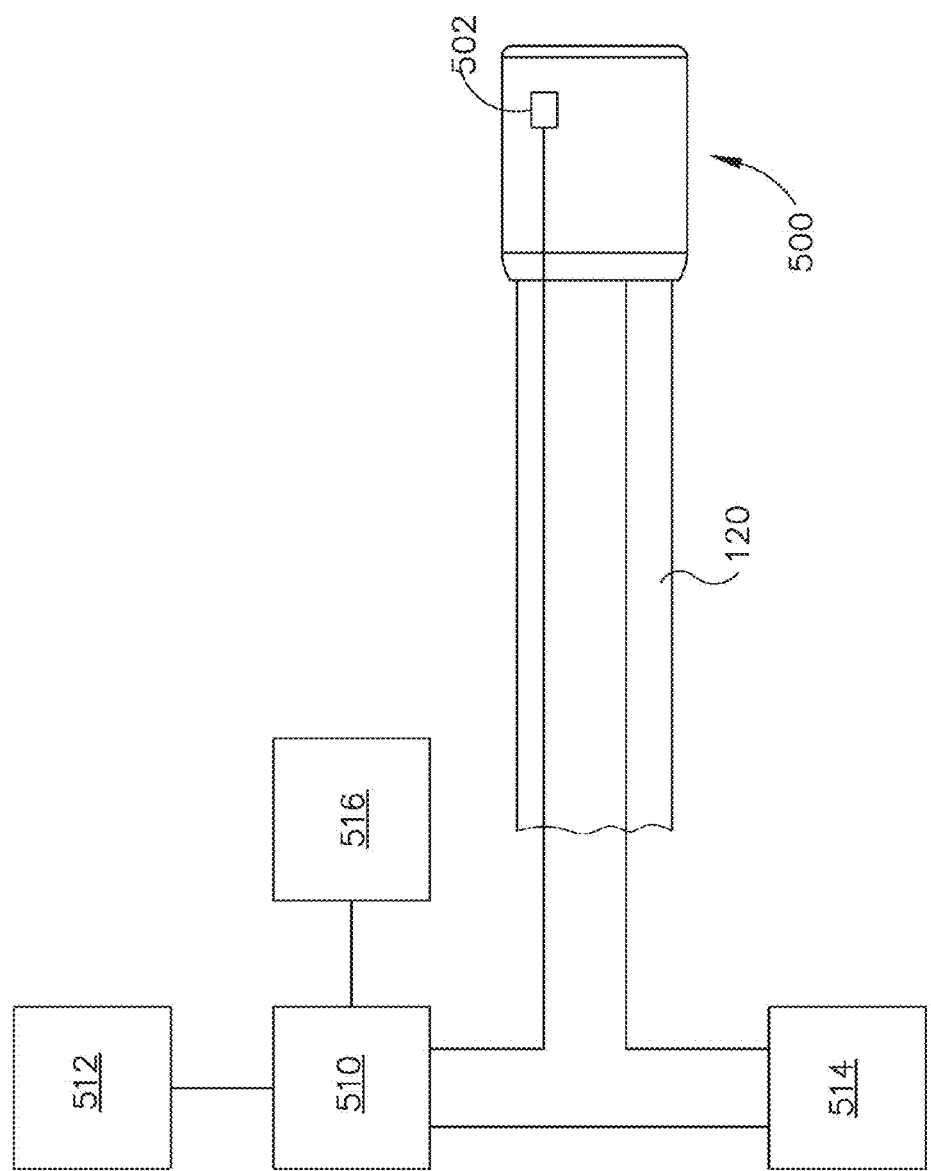
FIG. 23 depicts a side elevational view of a PETDD cannula having another exemplary alternative tip member.

FIG. 23 depicts another exemplary variation of PETDD (100) having a tip member (500) that includes a sensor (502). All of the other components in this variation are the same as those described above for PETDD (100). It should be understood that tip member (500) may have a substantially flat distal end as shown in FIG. 23, a beveled distal end like beveled tip member (300) shown in FIG. 21, or any other suitable configuration. In the present example, sensor (502) is in communication with a controller (510). Sensor (502) may communicate with controller (510) via one or more wires, one or more traces formed in or applied to cannula (120), wireless communication means, etc.

Controller (510) is in communication with a feedback device (512), a vacuum source (514), and a memory (516). Controller (510) is operable to selectively activate vacuum source (514) and/or feedback device (512) based on data from sensor (502) and memory (516) and/or in response to operator input. Controller (510) may comprise a microprocessor, ASIC, and/or various other components. Examples of components that may be incorporated into controller (510) will be described in greater detail below. In addition, other suitable components that may be incorporated into controller (510) will be apparent to those of ordinary skill in the art in view of the teachings herein. It should also be understood that one or more of the foregoing features may be omitted from PETDD (100) if desired. By way of example only, some other versions of PETDD (100) may lack sensor (502), feedback device (512), and memory (516). As another merely illustrative example, some other versions of PETDD (100) may lack vacuum source (514). Other suitable combinations and variations will be apparent to those of ordinary skill in the art in view of the teachings herein.

Vacuum source (514) is further coupled with cannula (120) and tip member (500), such that vacuum source (514) is operable to provide suction to tip member (500) based on instructions from controller (510). In some versions, this suction is used to assist in drawing the tympanic membrane (TM) against tip member (500), thereby promoting apposition between the tympanic membrane (TM) and tip member (500). In some uses of PETDD (100), an operator may wish to have vacuum source (514) deactivated during insertion of cannula (102) through the patient's ear canal; then activate vacuum source (514) via controller (510) after tip member (500) reaches the patient's tympanic membrane (TM). In drawing the tympanic membrane (TM) against tip member (500), the suction from vacuum source (514) may close any gaps that might otherwise remain from the operator's manual positioning of tip member (500).

In addition to or as an alternative to promoting apposition between tip member (500) and the tympanic membrane (TM), vacuum may be used to assist with sensing apposition between the tympanic membrane (TM) and tip member (500). For instance, sensor (502) may be operable to sense a physical parameter associated with fluid pressure in cannula (120) and tip member (500). With vacuum source (514) drawing suction as cannula (120) and tip member (500) are advanced toward the tympanic membrane (TM), the fluid pressure may remain substantially constant. However, as soon as tip member (500) achieves substantial apposition with the tympanic membrane (TM), the fluid pressure may suddenly and substantially drop. This pressure drop may be detected through sensor (502) and processed by controller (510). Various suitable forms that sensor (502) may take will be apparent to those of ordinary skill in the art in view of the teachings herein.

Controller (510) may monitor data from sensor (502) and compare it against one or more predetermined values stored in memory (516). When that data exceeds a threshold, falls below a threshold, or meets some other predetermined condition(s), controller (510) may trigger a predetermined response based on control logic/algorithms stored in memory (516). By way of example only, controller (510) may automatically deactivate vacuum source (514) in response to data from sensor (502). Such deactivation may occur upon the fluid pressure in cannula (120) dropping below a certain threshold. Alternatively, such deactivation may occur upon lapse of a certain time period following the fluid pressure of cannula (120) dropping below a certain threshold. As yet another merely illustrative example, controller (510) may automatically deactivate vacuum source (514) in response to deployment of PE tube (200). Of course, vacuum source (514) may simply be deactivated in response to user input directly from the operator of PETDD (100).

In some instances, controller (510) may activate feedback device (512) in response to data from sensor (502) exceeding a threshold, falling below a threshold, or satisfying some other predetermined condition(s). Feedback device (512) may provide any suitable perceivable feedback (e.g., audio, visual, and/or haptic feedback) to the operator of PETDD (100), to indicate to the operator that a significant event has occurred. For example, feedback device (512) may be used to inform the operator that the fluid pressure within cannula (120) has dropped below a threshold, thereby indicating to the operator that tip member (500) has achieved sufficient apposition with the tympanic membrane (TM). In addition or in the alternative, feedback device (512) may be used to inform the operator that PE tube (200) has been deployed. Other suitable events that may be alerted to the user through feedback device (512) will be apparent to those of ordinary skill in the art in view of the teachings herein. Similarly, various suitable forms that feedback device (512) may take will be apparent to those of ordinary skill in the art in view of the teachings herein.

In the example above, sensor (502) comprises a pressure sensor that is operable to detect fluid pressure within cannula (120). In addition or in the alternative, sensor (502) may be operable to detect strain in cannula (120) or tip member (500); and/or otherwise detect apposition between tip member (500) and the tympanic membrane (TM). By way of example only, sensor (502) may comprise a force sensor such as a strain gauge, inductive sensor, piezoelectric sensor and/or any other suitable type of sensor. Additional merely exemplary forms that sensor (502) may take are described in greater detail below. In the present example, sensor (502) is positioned near the distal end of tip member (500), such that sensor (502) may detect slight deformations that may occur in tip member (500) upon reaching sufficient apposition with the tympanic membrane (TM). It will be appreciated that sensor (502) may instead be positioned at any other suitable location along cannula (120). By way of example only, sensor (502) may be positioned at the interface of cannula (120) and tip member (500).

In versions where sensor (502) is operable to detect strain in cannula (120), controller (510) and feedback device (512) may be configured to provide the operator with real-time feedback associated with strain in cannula (120). This feedback may be interpreted by the user to indicate whether the operator should push harder distally on cannula (120). For instance, before tip member (500) reaches the tympanic membrane (TM), controller (510) may drive feedback device (512) to indicate to the operator that the operator needs to continue pushing distally on cannula (120). Once tip member (500) contacts the tympanic membrane (TM), sensor (502) may detect such contact; and controller (510) may responsively drive feedback device (512) to indicate to the operator that the operator has reached the tympanic membrane (TM). Feedback device (512) may further indicate to the operator that the operator needs to apply more or less force distally on cannula (120) in order to achieve proper apposition. Similarly, feedback device (512) may alert the operator when the distal force being applied to the tympanic membrane (TM) is excessive, thereby preventing potential damage to the tympanic membrane (TM). Other suitable ways in which sensor (502) and feedback device (512) may be used will be apparent to those of ordinary skill in the art in view of the teachings herein.

It should also be understood that two or more sensors (502) may be used in tip member (500), in cannula (120), and/or elsewhere. In versions with two or more sensors (502), such sensors (502) may detect the same kind of parameter (e.g., two sensors (502) detecting fluid pressure) and/or different parameters (e.g., one sensor (502) detecting fluid pressure and another sensor (502) detecting strain in tip member (500)). The control algorithms for controller (510) may be responsive to various permutations of data collected through a plurality of sensors (502). Various combinations of sensors (502) and types of control algorithms that may be based on data from two or more sensors (502) will be apparent to those of ordinary skill in the art in view of the teachings herein.

IV. Exemplary Apposition Sensing Features for Pressure Equalization Tube Delivery Instrument As noted above, a combination of a controller (510) and sensor (502) may be used to determine whether a suitable degree of apposition has been achieved between tip member (122, 500) and a tympanic membrane (TM). Controller (510) may process data from sensor (502) to drive a feedback device (512) to enable the operator to evaluate whether a suitable degree of apposition has been achieved between tip member (122, 500) and a tympanic membrane (TM). Information from feedback (512) may serve as a supplement or substitute for tactile feedback provided to the operator through PETDD (100) itself. The examples below include various forms that sensor (502) and controller (510) may take, in addition to or as an alternative to the forms described above. It should therefore be understood that the teachings below may be readily combined with the teachings above in various permutations. For instance, while several examples described below include feedback device (512) but not vacuum source (514), a vacuum source (514) may of course be readily incorporated into the below examples if desired. Still other suitable combinations and variations will be apparent to those of ordinary skill in the art in view of the teachings herein.

A. Exemplary Apposition Sensing with Resistance through Annular Electrode

Figure 24:
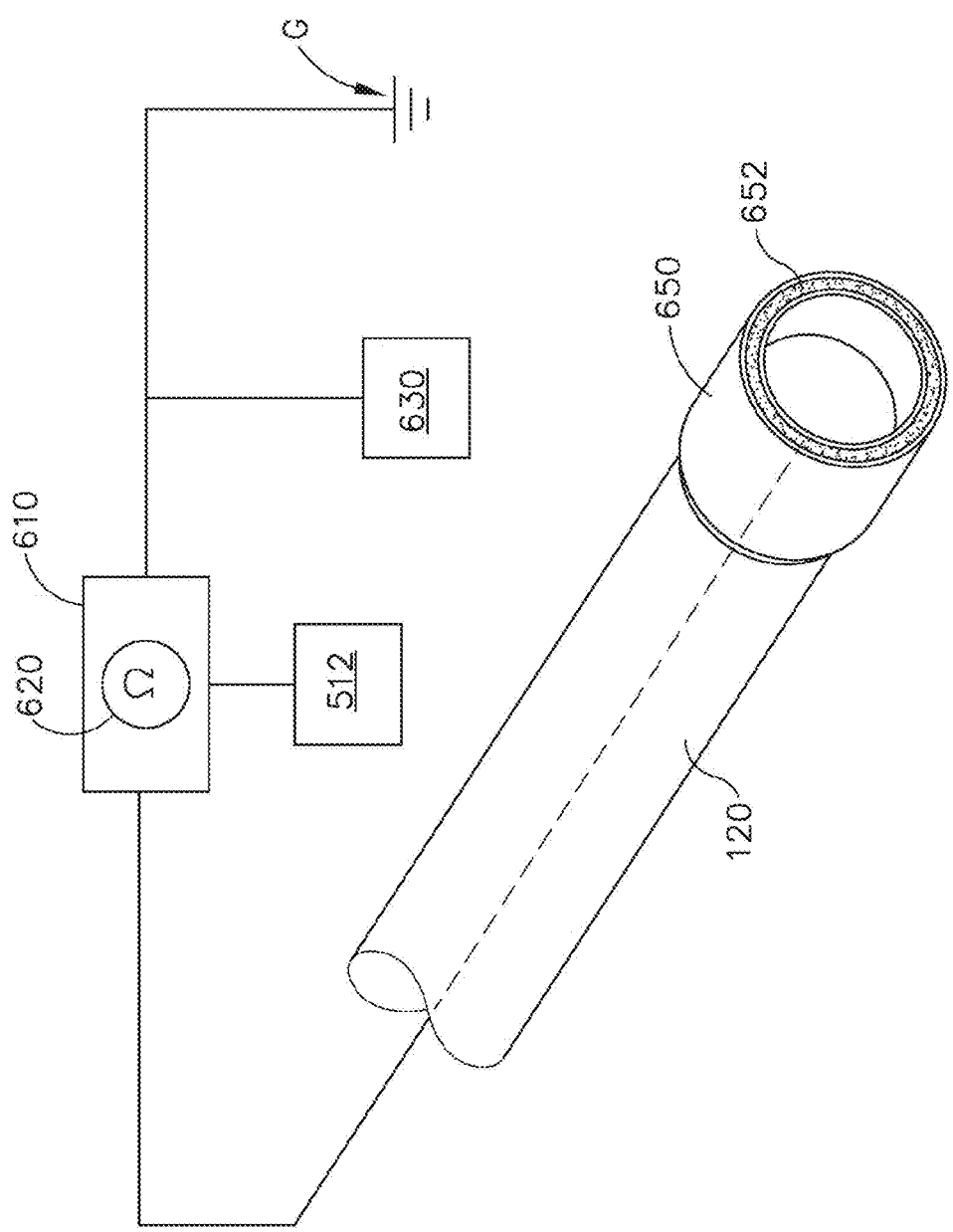
FIG. 24 depicts a perspective view of an exemplary PETDD cannula with an annular conductor at the distal tip, in combination with a ground pad and a controller.

FIG. 24 shows a variation of PETDD (100) having a tip member (650) that includes a distally facing annular electrode (652). Tip member (650) is formed of an electrically insulative material (e.g., plastic, etc.), such that electrode (652) is the only exposed conductive portion. In some versions, electrode (652) is formed as an annular trace in the distal edge of tip member (650). A controller (610) is in communication with electrode (652) and applies a voltage to electrode (652). By way of example only, a wire, trace, and/or other feature(s) may couple controller (610) with electrode (652). Controller (610) is also in communication with electrical ground (G), a ground pad (630), and feedback device (512). Ground pad (630) comprises a conventional ground pad that may be applied to an exposed portion of the patient's skin. Ground pad (630) thus provides a ground return path with the patient when electrode (652) contacts the patient while in an activated state.

Controller (610) also includes an ohmmeter (620). Ohmmeter (620) is placed in line between electrode (652) and both ground pad (630) and ground (G); such that ohmmeter (620) is configured to detect resistance (if direct current is used) or impedance (if alternating current is used) between electrode (652) and ground pad (630). The resistance or impedance detected through ohmmeter (620) may vary based on the degree of contact between electrode (652) and the patient. For instance, when conductive electrode (652) is not contacting the patient at all, ohmmeter (620) may register an infinite level of resistance/impedance, indicating an open circuit. When electrode (652) comes into physical contact with the tympanic membrane (TM), the resistance/impedance between electrode (652) and ground pad (630) is substantially reduced. The reduction in resistance/impedance may drop in accordance with the degree to which electrode (652) (and, hence, tip member (650)) contacts the tympanic membrane (TM). For instance, when electrode (652) (and, hence, tip member (650)) only partially contacts the tympanic membrane (TM), the resistance/impedance registered by ohmmeter (620) may drop slightly; but when electrode (652) (and, hence, tip member (650)) fully contacts the tympanic membrane (TM), the resistance/impedance registered by ohmmeter (620) may drop significantly. The resistance/impedance value registered by ohmmeter (620) may thus be inversely proportional to the degree of apposition between electrode (652) (and, hence, tip member (650)) and the tympanic membrane (TM), with high resistance/impedance values being associated with low apposition percentages and low resistance/impedance values being associated with high apposition percentages.

In some instances, feedback device (512) provides a real-time numerical value associated with sensed resistance/impedance, and the operator may determine when sufficient apposition has been achieved based on their reading of feedback device (512). In addition or in the alternative, feedback device (512) may comprise a set of LEDs that illuminate red when electrode (652)/tip member (650) is not contacting the tympanic membrane (TM), that illuminate yellow when electrode (652)/tip member (650) initially contacts the tympanic membrane (TM) but without an adequate degree of apposition, and that illuminate green when electrode (652)/tip member (650) achieves adequate apposition with the tympanic membrane (TM). Other suitable forms that feedback device (512) may take to provide visual feedback will be apparent to those of ordinary skill in the art in view of the teachings herein.

As another merely illustrative example, feedback device (512) may provide audible feedback to the operator. For instance, feedback device (512) may emit a buzz or an audible tone as soon as electrode (652)/tip member (650) achieves adequate apposition with the tympanic membrane (TM). As yet another merely illustrative example, feedback device (512) may start emitting a pattern of tones or beeps as soon as electrode (652)/tip member (650) initially contacts the tympanic membrane (TM) but without an adequate degree of apposition, with the pattern of tones increasing in frequency and/or volume as the degree of apposition increases. Other suitable forms that feedback device (512) may take to provide audible feedback will be apparent to those of ordinary skill in the art in view of the teachings herein. In addition to or as an alternative to audible and/or visual feedback, feedback device (512) may provide tactile feedback such as vibrations, etc. In some instances, PETDD (100) may be operable to automatically insert PE tube (200) into the tympanic membrane (TM) upon detection of sufficient apposition. Regardless of the form of feedback, suitable levels of resistance/impedance that may be set to trigger feedback device (512) will be apparent to those of ordinary skill in the art in view of the teachings herein.

B. Exemplary Apposition Sensing with Resistance Through Discrete Electrodes

Figure 25:
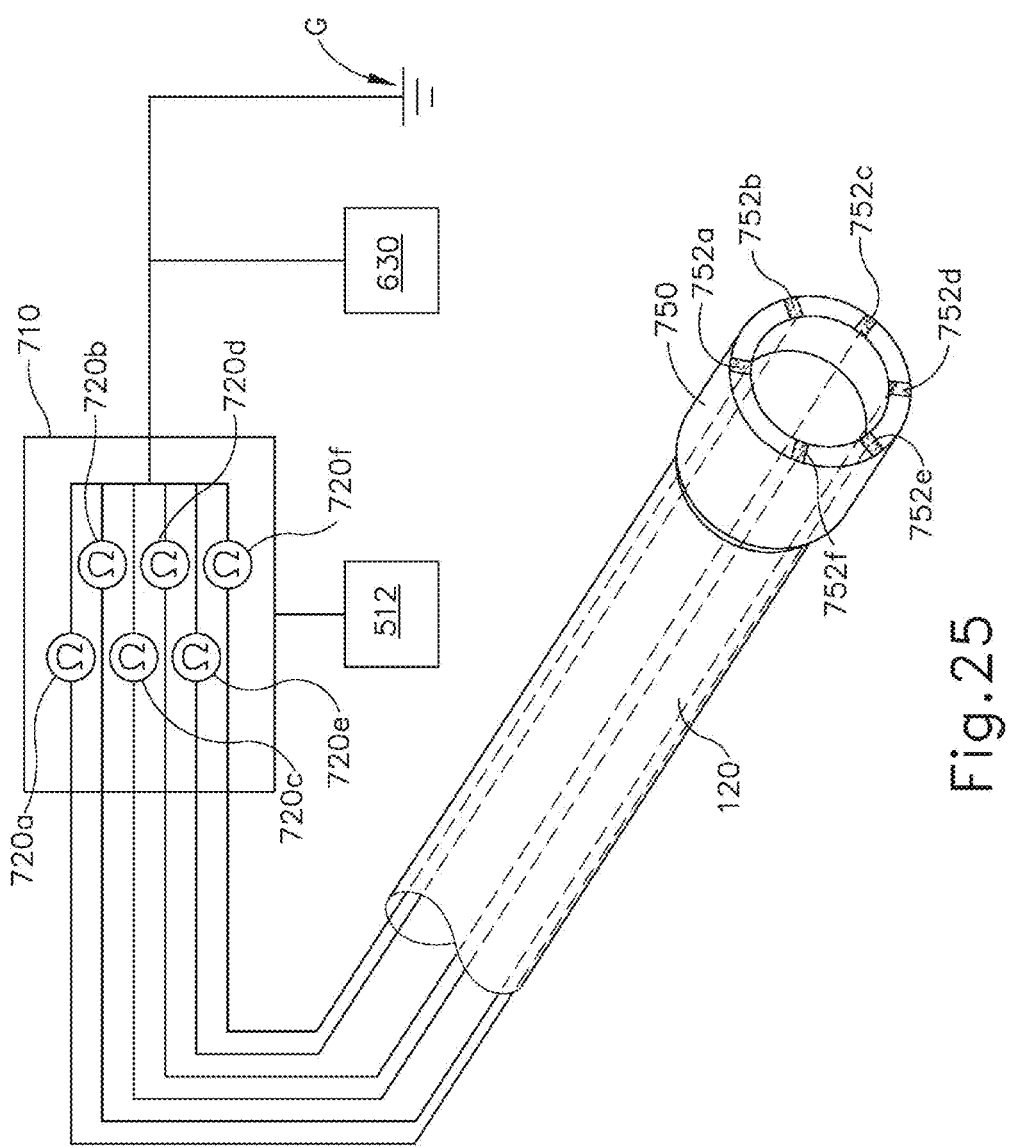
FIG. 25 depicts a perspective view of an exemplary PETDD cannula with a plurality of discrete conductors at the distal tip, in combination with a ground pad and a controller.

FIG. 25 shows a variation of PETDD (100) having a tip member (750) that includes a plurality of distally facing discrete electrodes (752a, 752b, 752c, 752d, 752e, 752f). Electrodes (752a, 752b, 752c, 752d, 752e, 752f) are arranged in an annular array. While six electrodes (752a, 752b, 752c, 752d, 752e, 752f) are shown, it should be understood that any other suitable number may be used in any other suitable arrangement. Electrodes (752a, 752b, 752c, 752d, 752e, 752f) are isolated from each other in this example. Tip member (750) is formed of an electrically insulative material (e.g., plastic, etc.), such that electrodes (752a, 752b, 752c, 752d, 752e, 752f) are the only exposed conductive portions. In some versions, each electrode (752a, 752b, 752c, 752d, 752e, 752f) is formed as a discrete trace in the distal edge of tip member (750). In some other versions each electrode (752a, 752b, 752c, 752d, 752e, 752f) is formed by exposing a portion of wire wrapped over the distal edge of tip member (750). Other suitable ways in which electrodes (752a, 752b, 752c, 752d, 752e, 752f) may be formed will be apparent to those of ordinary skill in the art in view of the teachings herein.

A controller (710) is in communication with electrodes (752a, 752b, 752c, 752d, 752e, 752f) and applies a voltage to each electrode (752a, 752b, 752c, 752d, 752e, 752f). By way of example only, wires, traces, and/or other feature(s) may couple controller (710) with electrodes (752a, 752b, 752c, 752d, 752e, 752f). Controller (710) is also in communication with electrical ground (G), a ground pad (630), and feedback device (512). Ground pad (630) comprises a conventional ground pad that may be applied to an exposed portion of the patient's skin. Ground pad (630) thus provides a ground return path with the patient when any electrode (752a, 752b, 752c, 752d, 752e, 752f) contacts the patient while in an activated state.

Controller (710) also includes a plurality of ohmmeters (720a, 720b, 720c, 720d, 720e, 7200. Each ohmmeter (720a, 720b, 720c, 720d, 720e, 7200 is placed in line between a corresponding electrode (752a, 752b, 752c, 752d, 752e, 7520 and both ground pad (630) and ground (G); such that each ohmmeter (720a, 720b, 720c, 720d, 720e, 7200 is configured to detect resistance (if direct current is used) or impedance (if alternating current is used) between a particular corresponding electrode (752a, 752b, 752c, 752d, 752e, 7520 and ground pad (630). The resistance or impedance detected through each ohmmeter (720a, 720b, 720c, 720d, 720e, 7200 may vary based on the degree of contact between the corresponding electrode (752a, 752b, 752c, 752d, 752e, 7520 and the patient. For instance, when a given electrode (752a, 752b, 752c, 752d, 752e, 7520 is not contacting the patient at all, the corresponding ohmmeter (720a, 720b, 720c, 720d, 720e, 720f) may register an infinite level of resistance/impedance, indicating an open circuit. When the same electrode (752a, 752b, 752c, 752d, 752e, 7520 comes into physical contact with the tympanic membrane (TM), the resistance/impedance between that electrode (752a, 752b, 752c, 752d, 752e, 752f) and ground pad (630) is substantially reduced.

Controller (710) may determine the degree of apposition based on the number of electrodes (752a, 752b, 752c, 752d, 752e, 752f) showing a substantial reduction in resistance/impedance, as measured through ohmmeters (720a, 720b, 720c, 720d, 720e, 720f). For instance, controller (710) may activate feedback device (512) based on the number of electrodes (752a, 752b, 752c, 752d, 752e, 752f) showing a substantial reduction in resistance/impedance. In some such versions, the triggering threshold may thus be the number of electrodes (752a, 752b, 752c, 752d, 752e, 752f) contacting the tympanic membrane (TM); rather than a particular resistance/impedance value alone serving as a triggering threshold. Of course, feedback device (512) in this context may be configured and operable in accordance with any of the teachings herein relating to feedback device (512).

Figure 26:
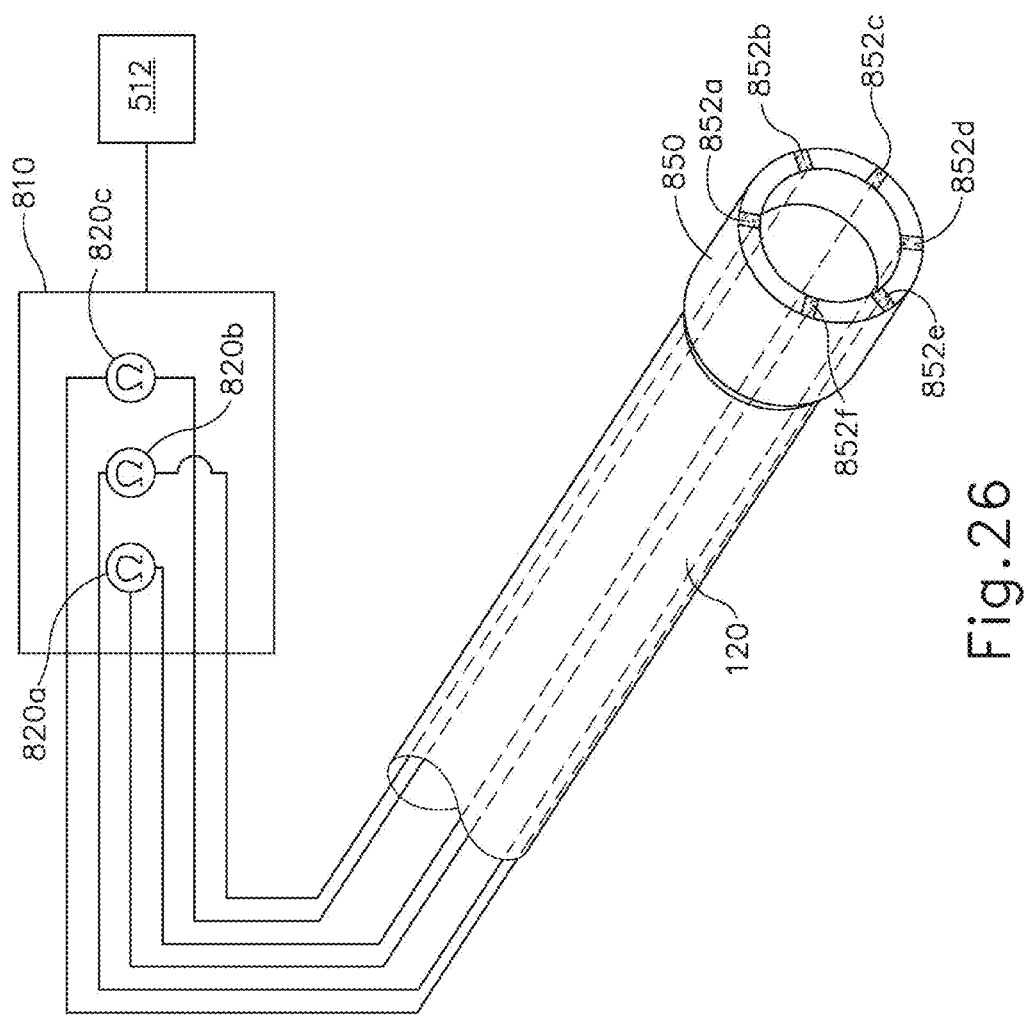
FIG. 26 depicts a perspective view of an exemplary PETDD cannula with a plurality of discrete conductor pairs at the distal tip, in combination with a controller.

FIG. 26 shows another variation of PETDD (100) having a tip member (850) that includes a plurality of distally facing discrete electrodes (852a, 852b, 852c, 852d, 852e, 852f). Electrodes (852a, 852b, 852c, 852d, 852e, 852f) are arranged in an annular array. While six electrodes (852a, 852b, 852c, 852d, 852e, 852f) are shown, it should be understood that any other suitable number may be used in any other suitable arrangement. Electrodes (852a, 852b, 852c, 852d, 852e, 852f) form pairs in this example. In particular, electrodes (852*a* 852*d*) form a pair, electrodes (852*b*, 852*e*) form a pair, and electrodes (852*c*, 852*f*) form a pair. The electrodes (852*a*, 852*b*, 852*c*, 852*d*, 852*e*, 852*f*) of each pair are located in diametrically opposing positions along the outer perimeter of the distal face of tip member (850). Tip member (850) is formed of an electrically insulative material (e.g., plastic, etc.), such that electrodes (852*a*, 852*b*, 852*c*, 852*d*, 852*e*, 852*f*) are the only exposed conductive portions. In some versions, each electrode (852*a*, 852*b*, 852*c*, 852*d*, 852*e*, 852*f*) is formed as a discrete trace in the distal edge of tip member (850). In some other versions each electrode (852*a*, 852*b*, 852*c*, 852*d*, 852*e*, 852*f*) is formed by exposing a portion of wire wrapped over the distal edge of tip member (850). Other suitable ways in which electrodes (852*a*, 852*b*, 852*c*, 852*d*, 852*e*, 852*f*) may be formed will be apparent to those of ordinary skill in the art in view of the teachings herein.

A controller (810) is in communication with electrodes (852*a*, 852*b*, 852*c*, 852*d*, 852*e*, 8520 and applies a voltage to each pair of electrodes (852*a*, 852*b*, 852*c*, 852*d*, 852*e*, 8520. By way of example only, wires, traces, and/or other feature(s) may couple controller (810) with electrodes (852*a*, 852*b*, 852*c*, 852*d*, 852*e*, 8520. Controller (810) is also in communication with feedback device (512). Controller (810) also includes a plurality of ohmmeters (820*a*, 820*b*, 820*c*). Each ohmmeter (820*a*, 820*b*, 820*c*) is associated with a particular pair of electrodes (852*a*, 852*b*, 852*c*, 852*d*, 852*e*, 8520. In particular, ohmmeter (820*a*) is coupled with electrodes (852*c*, 8520, ohmmeter (820*b*) is coupled with electrodes (852*a*, 8520, and ohmmeter (820*c*) is coupled with electrodes (852*b*, 852*e*). Each ohmmeter (820, 820*b*, 820*c*) is configured to detect resistance (if direct current is used) or impedance (if alternating current is used) between the electrodes (852*a*, 852*b*, 852*c*, 852*d*, 852*e*, 8520 of the pair associated with ohmmeter (820*a*, 820*b*, 820*c*). Thus, ohmmeter (820*a*) is configured to detect resistance/impedance between electrodes (852*c*, 8520, ohmmeter (820*b*) is configured to detect resistance/impedance between electrodes (852*a*, 8520, and ohmmeter (820*c*) is configured to detect resistance/impedance between electrodes (852*b*, 852*e*). The resistance or impedance detected through each ohmmeter (820*a*, 820*b*, 820*c*) may vary based on the degree of contact between the corresponding electrodes (852*a*, 852*b*, 852*c*, 852*d*, 852*e*, 8520 and the patient. For instance, when a given electrode (852*a*, 852*b*, 852*c*, 852*d*, 852*e*, 8520 pair is not contacting the patient at all, the corresponding ohmmeter (820*a*, 820*b*, 820*c*) may register an infinite level of resistance/impedance, indicating an open circuit. When the same electrode (852*a*, 852*b*, 852*c*, 852*d*, 852*e*, 8520 pair comes into physical contact with the tympanic membrane (TM), the resistance/impedance between the electrodes (852*a*, 852*b*, 852*c*, 852*d*, 852*e*, 8520 of that pair is substantially reduced.

Controller (810) may determine the degree of apposition based on the number of electrode (852*a*, 852*b*, 852*c*, 852*d*, 852*e*, 8520 pairs showing a substantial reduction in resistance/impedance, as measured through ohmmeters (820*a*, 820*b*, 820*c*). For instance, controller (810) may activate feedback device (512) based on the number of electrode (852*a*, 852*b*, 852*c*, 852*d*, 852*e*, 8520 pairs showing a substantial reduction in resistance/impedance. In some such versions, the triggering threshold may thus be the number of electrode (852*a*, 852*b*, 852*c*, 852*d*, 852*e*, 8520 pairs contacting the tympanic membrane (TM); rather than a particular resistance/impedance value alone serving as a triggering threshold. Of course, feedback device (512) in this context may be configured and operable in accordance with any of the teachings herein relating to feedback device (512). It should also be understood that controller may monitor inductance of electrode (852*a*, 852*b*, 852*c*, 852*d*, 852*e*, 8520 pairs in addition to or in lieu of monitoring resistance/impedance.

C. Exemplary Apposition Sensing with Capacitance Through Annular Electrode

Figure 27:
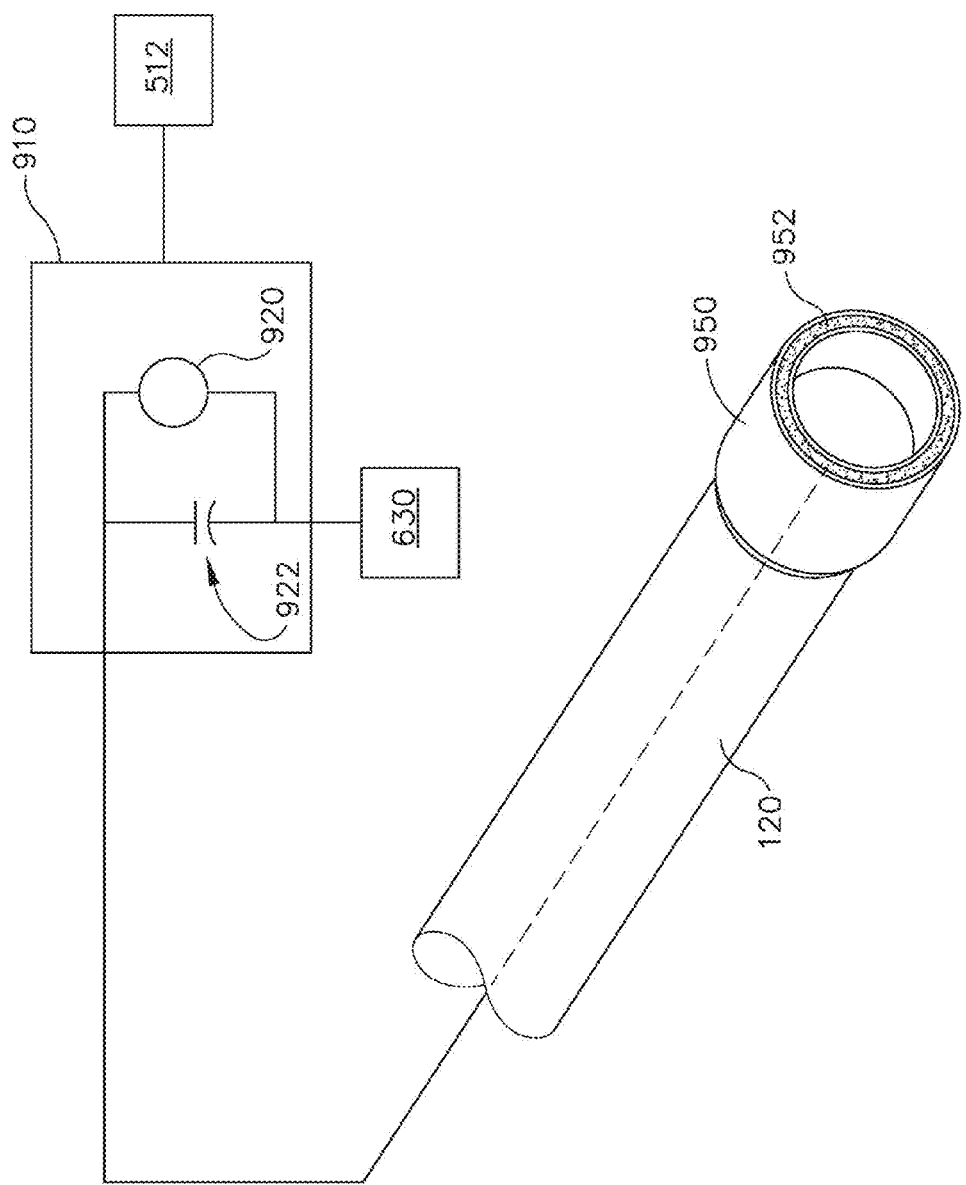
FIG. 27 depicts a perspective view of an exemplary PETDD cannula with an annular conductor at the distal tip, in combination with a controller.
Figure 30:
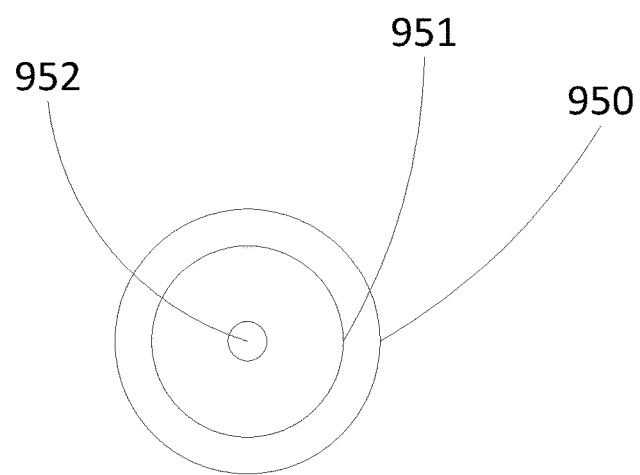
FIG. 30 shows a schematic representation of a distal end view of a shaft and an electrode disposed within an inner diameter of the shaft.

FIG. 27 shows another variation of PETDD (100) having a tip member (950) that includes a distally facing annular electrode (952). Tip member (950) is formed of an electrically insulative material (e.g., plastic, etc.), such that electrode (952) is the only exposed conductive portion. In some versions, electrode (952) is formed as an annular trace in the distal edge of tip member (950). Tip member (950) may also include an annular ridge protruding about the outer perimeter of electrode (952), which may act as a shield to prevent tissue that is positioned laterally relative to electrode (952) from affecting capacitance measurements as described below. As another merely illustrative variation, as shown, for example, FIG. 30, electrode (952) may be formed by a rod or other feature located somewhere within the inner diameter (951) of tip member (950).

A controller (910) is in communication with electrode (952) and applies a voltage to electrode (952). By way of example only, a wire, trace, and/or other feature(s) may couple controller (910) with electrode (952). Controller (910) is also in communication with a ground pad (630), and feedback device (512). Ground pad (630) comprises a conventional ground pad that may be applied to an exposed portion of the patient's skin. Ground pad (630) thus provides a ground return path with the patient when electrode (952) contacts the patient while in an activated state.

Controller (910) also includes a capacitance meter (920) and a capacitor (922). It should be understood that capacitor (922) is merely optional. Capacitance meter (920) is configured to detect the capacitance formed between electrode (952) and the tympanic membrane (TM). The capacitance detected through capacitance meter (920) may thus vary based on the degree of contact between electrode (952) and the patient. For instance, the capacitance formed between electrode (952) and the tympanic membrane (TM) may drop significantly as electrode (952) (and, hence, tip member (950)) comes into contact with the tympanic membrane (TM). In response to this drop in capacitance, controller (910) may activate feedback device (512) in accordance with any of the teachings herein relating to feedback device (512).

D. Exemplary Apposition Sensing with Light Pipes

Figure 28:
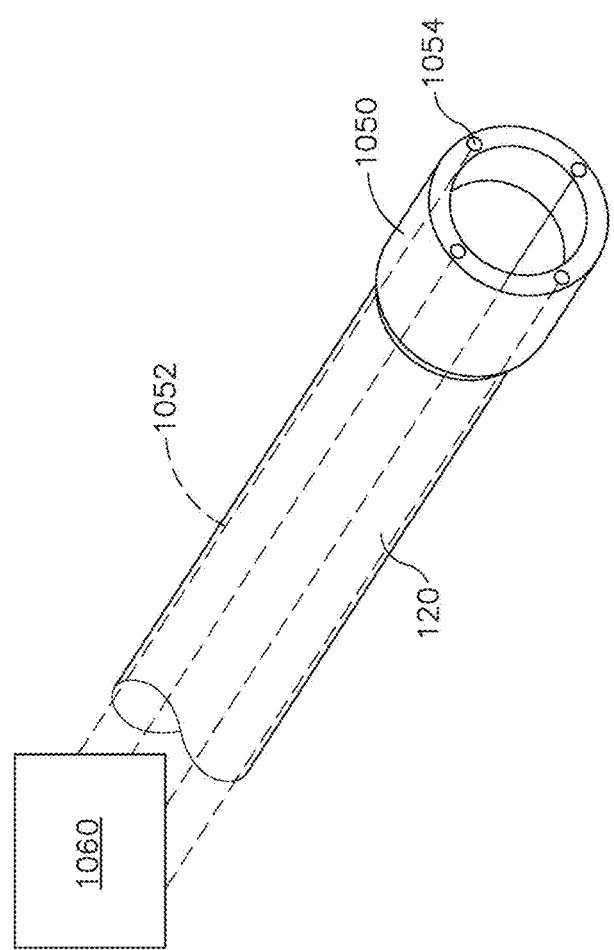
FIG. 28 depicts a perspective view of an exemplary PETDD cannula with a plurality of light pipes terminating at the distal tip.

FIG. 28 shows a variation of PETDD (100) where a series of light pipes (1052) extend along cannula (120) and through a tip member (1050). Light pipes (1052) distally terminate at distal ends (1054) located at the distal edge of tip member (1050). Light pipes (1052) are optically coupled with light source (1060) and are operable to convey light from light source (1060) to distal ends (1054). By way of example only, light pipes (1052) may be coupled with light source (1060) via optical fibers and/or any other suitable type of structures. While four light pipes (1052) are shown, it should be understood that any other suitable number of light pipes (1052) may be provided. Light pipes (1052) are angularly arrayed equidistantly about the perimeter of the distal edge of tip member (1050) in this example, though it should be understood that any other suitable arrangement may be used.

In some versions, light conveyed through light pipes (1052) is externally visible along at least part of the length of light pipes (1052). For instance, a visible light may be seen through portion of light pipes (1052) extending through tip member (1050). In some such versions, the distal portions of light pipes (1052) are formed by channels within tip member (1050). In the present example, light pipes (1052) emit visible light through distal ends (1054). This visible light may be transmitted to the tympanic membrane (TM) as the operator inserts cannula (120) through the patient's ear canal. The light may appear as four dots on the tympanic membrane (TM). As tip member (1050) engages the tympanic membrane (TM), these projected dots may eventually darken. Thus, the operator may receive visual feedback indicating the degree of apposition between tip member (1050) and the tympanic membrane (TM), based on the degree to which light from light pipes (1052) has been darkened by contact with the tympanic membrane (TM). Other suitable ways in which light pipes (1052) may be incorporated into PETDD (100) will be apparent to those of ordinary skill in the art in view of the teachings herein.

E. Exemplary Apposition Sensing Through Enhanced Visualization

Figure 29:
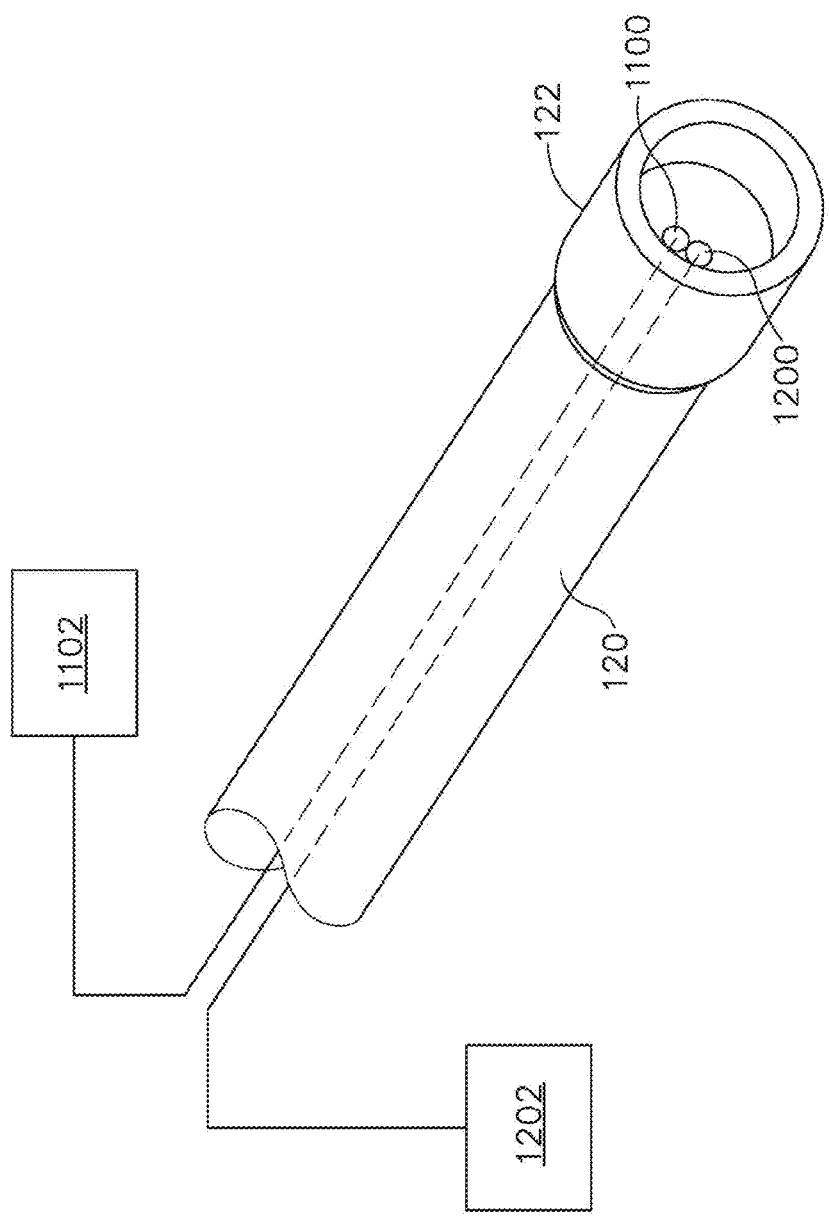
FIG. 29 depicts a perspective view of an exemplary PETDD cannula with an integrated light fiber and imaging device.

FIG. 29 shows a variation of PETDD (100) where a light fiber (1100) and an imaging device (1200) extend through cannula (120) to tip member (122). Light fiber (1100) and imaging device (1200) terminate just proximal to the distal edge of tip member (122). Light fiber (1110) is coupled with a light source (1102). Light fiber (1100) may be coupled with light source (1102) using any suitable type of structures. While just one light fiber (1100) is shown, it should be understood that any other suitable number of light fibers (1100) may be provided. Light fiber (1100) is positioned and operable to illuminate the tympanic membrane (TM) right at the tympanostomy site. It should be understood that light fiber (1100) may even illuminate the tympanostomy site when tip member (122) is in full apposition with the tympanic membrane (TM).

Imaging device (1200) may comprise any suitable type of scope, imaging fiber, etc. that is operable to capture and transmit images. Various suitable forms that imaging device (1200) may take will be apparent to those of ordinary skill in the art in view of the teachings herein. Imaging device (1200) is in communication with a display device (1202). Display device (1202) may comprise a video display screen, a set of wearable loupes, and/or any other suitable device. Various suitable forms that display device (1200) may take, as well as various suitable ways in which imaging device (1200) may be coupled with display device (1202), will be apparent to those of ordinary skill in the art in view of the teachings herein. Imaging device (1200) is positioned and operable to capture real-time video images of the tympanostomy site as cannula (120) is being inserted down the patient's ear canal. It should be understood that imaging device (1200) may even capture video images of the tympanostomy site when tip member (122) is in full apposition with the tympanic membrane (TM). Thus, with the combination of light projected from light fiber (1100) and video provided by imaging device (1200) and display device (1202), an operator may receive helpful real-time visual feedback indicating the positioning of tip member (122) and degree of apposition between tip member (122) and the tympanic membrane. Due to the positioning of imaging device (1200) in this example, this visual feedback may be more useful than visual feedback that might otherwise be provided through an imaging device that is positioned external to cannula (120).

V. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

The invention claimed is:
1. An apparatus comprising:
 (a) a shaft assembly having a distal end having an annular distal face, wherein the shaft assembly comprises:
  (i) a cannula, and
  (ii) a pusher operable to translate relative to the cannula;
 (b) a pressure equalization tube positioned within the shaft assembly, wherein the pusher is operable to drive the pressure equalization tube out of the shaft assembly; and

(c) at least one exposed electrode positioned at the distal end of the shaft assembly, wherein the at least one exposed electrode is (i) operable to detect a physical parameter associated with the distal end of the shaft assembly as the distal end of the shaft assembly is advanced toward and into engagement with a tympanic membrane and (ii) comprises an annular electrode disposed on the annular distal face of the distal end of the shaft assembly.

2. The apparatus of claim 1, further comprising a controller in communication with the at least one exposed electrode.

3. The apparatus of claim 2, further comprising a ground pad, wherein the controller is operable to detect electrical resistance or impedance between the at least one exposed electrode and the ground pad.

4. The apparatus of claim 2, wherein the controller is operable to detect a capacitance associated with the at least one exposed electrode.

5. The apparatus of claim 4, wherein the controller is operable to control a feedback device based on the capacitance associated with the at least one exposed electrode,
the feedback device operable to indicate when the distal end of the shaft assembly engages with the tympanic membrane.

6. The apparatus of claim 2, wherein the controller includes a capacitance meter, the capacitance meter configured to detect the capacitance between the at least one exposed electrode and the tympanic membrane.

7. The apparatus of claim 2, wherein the controller includes a capacitor.

8. The apparatus of claim 1, further comprising a user feedback feature, wherein the user feedback feature is operable to alert an operator to one or more conditions associated with engagement between the distal end of the shaft assembly and the tympanic membrane based on information from a sensor.

9. The apparatus of claim 1, further comprising a vacuum source operable to draw a tympanic membrane against the distal end of the shaft assembly.

10. The apparatus of claim 9, wherein the pusher defines a lumen, wherein the vacuum source is operable to communicate suction through the lumen of the pusher.

11. The apparatus of claim 9, further comprising a controller, wherein the controller is in communication with the at least one exposed electrode, wherein the controller is in further communication with the vacuum source, wherein the controller is configured to deactivate the vacuum source based at least in part on information from a sensor indicating one or more conditions associated with engagement between the distal end of the shaft assembly and a tympanic membrane.

12. The apparatus of claim 1, wherein the distal end of the shaft assembly is beveled.

13. The apparatus of claim 1, further comprising an imaging device disposed within the shaft assembly.

14. The apparatus of claim 1, wherein the distal end of the shaft assembly includes an annular ridge formed of an electrically insulative material, the annular ridge protruding about the outer perimeter of the annular electrode.

15. An apparatus comprising:
(a) a shaft assembly having a distal end having an annular distal face, wherein the shaft assembly comprises:
(i) a cannula, and
(ii) a pusher operable to translate relative to the cannula;
(b) a pressure equalization tube positioned within the shaft assembly, wherein the pusher is operable to drive the pressure equalization tube out of the shaft assembly;
(c) at least one exposed electrode comprising an annular electrode disposed on the annular distal face of the distal end of the shaft assembly; and
(d) a controller, the controller operable to apply a voltage to the at least one exposed electrode such that the controller can detect a capacitance formed between the at least one electrode and a tympanic membrane.

16. The apparatus of claim 15, further comprising a user feedback device operable to alert an operator of a change in the capacitance formed between the at least one exposed electrode and the tympanic membrane.

17. A method comprising:
(a) disposing a shaft assembly proximate a tympanic membrane of a patient such that a capacitance is formed by a distal end of the shaft assembly and the tympanic membrane, the distal end having an annular distal face, the shaft assembly comprising:
(i) a cannula,
(ii) a pusher operable to translate relative to the cannula, and
(iii) at least one exposed electrode including an annular electrode disposed on the annular distal face of the distal end of the shaft assembly;
(b) advancing the shaft assembly into engagement with the tympanic membrane of the patient;
(c) detecting a change in the capacitance formed by the distal end of the shaft assembly and the tympanic membrane; and
(d) operating, in response to the detecting, the pusher of the shaft assembly to drive a pressure equalization tube positioned within the shaft assembly out of the shaft assembly.

18. An apparatus comprising:
(a) a shaft assembly having a distal end, wherein the shaft assembly comprises:
(i) a cannula, and
(ii) a pusher operable to translate relative to the cannula;
(b) a pressure equalization tube positioned within the shaft assembly, wherein the pusher is operable to drive the pressure equalization tube out of the shaft assembly; and
(c) at least one exposed electrode positioned at the distal end of the shaft assembly, wherein the at least one exposed electrode is (i) operable to detect a physical parameter associated with the distal end of the shaft assembly as the distal end of the shaft assembly is advanced toward and into engagement with a tympanic membrane and (ii) disposed within an inner diameter of the distal end of the shaft assembly.

* * * * *